(12) United States Patent
Vandersickel et al.

(10) Patent No.: US 11,612,323 B2
(45) Date of Patent: Mar. 28, 2023

(54) DETECTION OF ROTATIONAL ACTIVITY IN CARDIAC ELECTROPHYSIOLOGY

(71) Applicant: UNIVERSITEIT GENT, Ghent (BE)

(72) Inventors: Nele Vandersickel, Mariakerke (BE); Enid Van Nieuwenhuyse, De Pinte (BE); Alexander V. Panfilov, Bilthoven (NL)

(73) Assignee: UNIVERSITEIT GENT, Ghent (BE)

( * ) Notice: Subject to any disclaimer, the term of this patent is extended or adjusted under 35 U.S.C. 154(b) by 243 days.

(21) Appl. No.: 16/767,866

(22) PCT Filed: Nov. 28, 2018

(86) PCT No.: PCT/EP2018/082799
§ 371 (c)(1),
(2) Date: May 28, 2020

(87) PCT Pub. No.: WO2019/105986
PCT Pub. Date: Jun. 6, 2019

(65) Prior Publication Data
US 2020/0367751 A1 Nov. 26, 2020

(30) Foreign Application Priority Data

Nov. 29, 2017 (EP) .................................. 17204434
Jun. 29, 2018 (EP) .................................. 18180791

(51) Int. Cl.
*A61B 5/00* (2006.01)
*G16H 50/20* (2018.01)
(Continued)

(52) U.S. Cl.
CPC ............ *A61B 5/0044* (2013.01); *A61B 5/316* (2021.01); *A61B 5/339* (2021.01); *G16H 50/20* (2018.01)

(58) Field of Classification Search
CPC ....... A61B 5/0044; A61B 5/316; A61B 5/339; G16H 50/20
See application file for complete search history.

(56) References Cited

U.S. PATENT DOCUMENTS 8,700,140 B2    4/2014  Narayan et al.
2011/0251505 A1 10/2011 Narayan et al.
(Continued)

FOREIGN PATENT DOCUMENTS

WO    2015/153797 A1    10/2015

OTHER PUBLICATIONS

Extended European Search Report from corresponding EP Application No. 17204434.9, dated Mar. 28, 2018.
(Continued)

*Primary Examiner* — David D Davis
(74) *Attorney, Agent, or Firm* — Workman Nydegger

(57) ABSTRACT

A device for detecting points and/or regions of rotational electrophysiological activity in or on a heart comprises an input for receiving spatiotemporal electrophysiological data corresponding to a plurality of spatial locations in or on the heart, a time feature extractor for providing time values indicative of times of occurrence of a predetermined feature of a plurality of electric potential waveforms at the spatial location, a mapping unit for providing pairs of adjacent spatial locations; a directed graph generator for generating a directed graph comprising directed edges; a topological feature analyzer.

16 Claims, 15 Drawing Sheets

(51) Int. Cl.
*A61B 5/316* (2021.01)
*A61B 5/339* (2021.01)

(56) References Cited

U.S. PATENT DOCUMENTS

| | | | | |
|---|---|---|---|---|
| 2014/0371609 | A1* | 12/2014 | Narayan | A61B 18/12 |
| | | | | 600/508 |
| 2017/0055864 | A1* | 3/2017 | Han | A61B 5/349 |
| 2017/0319089 | A1* | 11/2017 | Lou | A61B 5/7278 |

OTHER PUBLICATIONS

International Search Report and Written Opinion from PCT Application No. PCT/EP2018/082799, dated Mar. 21, 2019.
Cantwell et al., "Techniques for Automated Local Activation Time Annotation and Conduction Velocity Estimation in Cardiac Mapping", Computers in Biology and Medicine, Apr. 29, 2015, 18 pages.
Deno et al., "Orientation-Independent Catheter-Based Characterization of Myocardial Activation", IEEE Transactions on Biomedical Engineering, vol. 64, No. 5, May 1, 2017, pp. 1067-1077.
Haddad et al, "Novel Algorithmic Methods in Mapping of Atrial and Ventricular Tachycardia", Circulation: Arrhythmia and Electrophysiology, Jun. 17, 2014, pp. 463-472.
Konings et al., "High-Density Mapping of Electrically Induced Atrial Fibrillation in Humans" Circulation, vol. 89, No. 4, Apr. 1, 1994, pp. 1665-1680.
Tusscher et al., "Altemans and Spiral Breakup in a Human Ventricular Tissue Model", American Journal of Physiology—Heart and Circulatory Physiology, vol. 291, No. 3, Mar. 24, 2006, pp. H1088-H1100.
Bang-Jensen, et al., "Digraphs Theory, Algorithms and Applications", Springer-Verlag, Aug. 15, 2007, 772 pages.

* cited by examiner

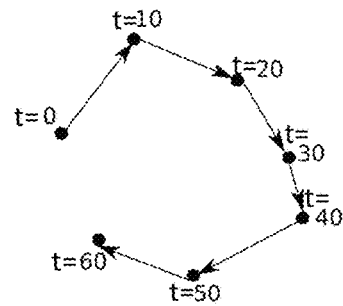
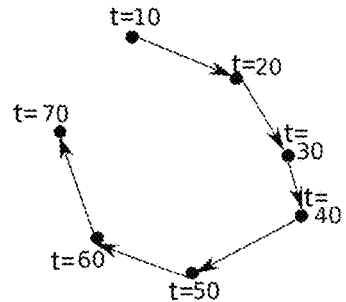
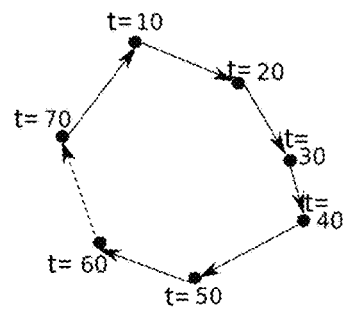
FIG 25　　　　　FIG 26　　　　　FIG 27
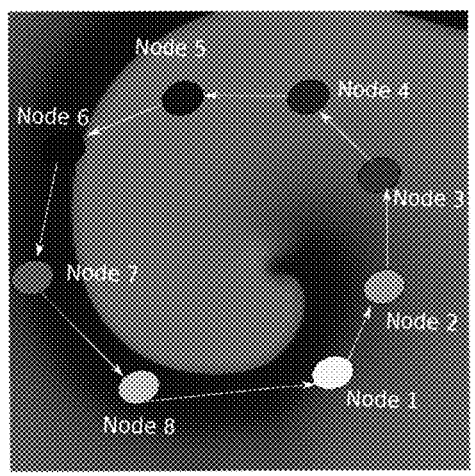
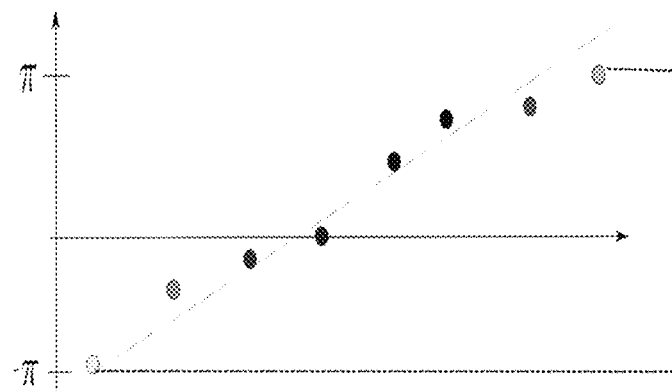
FIG 28　　　　　　　　　FIG 29
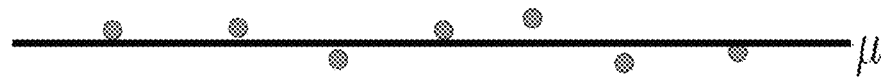
FIG 30

DETECTION OF ROTATIONAL ACTIVITY IN CARDIAC ELECTROPHYSIOLOGY

FIELD OF THE INVENTION

The invention relates to the field of automated analysis of spatiotemporal electrophysiological data gathered in or on the heart. More specifically it relates to a device and method for detecting points and/or regions of interest in the heart that are indicative of cardiac arrhythmia symptoms.

BACKGROUND OF THE INVENTION

Cardiac arrhythmia is a condition in which the heartbeat is irregular and/or has an abnormal frequency, e.g. in which an abnormal resting heart rate can be observed. It is known in the art that such arrhythmias can be caused by an abnormal electrical conduction in the heart or near the heart, i.e. by abnormalities in the action potential impulse propagation system that drives the heart contraction in a synchronized manner.

Under normal conditions, a heart beat originates from the sinoatrial node in the right atrium, upon which a propagating excitation front causes a contraction of both atria. Then, via the atrioventricular node, which connects the atria to the ventricles in the electrical conduction system of the heart, the bundle of Hys and the Purkinje fibers, the propagating excitation causes a complete contraction cycle of the heart.

Abnormalities in this conduction system, which may cause cardiac arrhythmia symptoms, include focal activity and/or rotational activity, e.g. re-entrant activity such as atrial fibrillation, ventricular fibrillation and ventricular tachycardia.

In focal activity, ectopic foci may disrupt the normal action potential propagation. Such ectopic focus refers to a tissue part that initiates an impulse without being excited by the normal propagating excitation front initiated by the sinoatrial node. This type of arrhythmia comprises triggered activity phenomena, such as early afterdepolarization (EAD) and delayed afterdepolarization (DAD).

In re-entrant activity, the excitation wave propagates along a loop. In most of the cases, this may occur as a result of an unidirectional block of the propagation, which can be due to a heterogeneity of the refractory period or abnormal impulse conduction. These rotational phenomena can be classified into anatomical re-entry and functional re-entry activities. In anatomical re-entry, the electrical wave may propagate around an inexcitable obstacle, such as scar tissue, while in functional re-entry, the rotation occurs around the refractory tail of the wave, i.e. without requiring a propagation obstacle.

Atrial fibrillation (AF) is a common type of cardiac arrhythmia, which is often even considered as the most common arrhythmia in clinical practice. It is widely accepted that AF is maintained by rotational activity. It has been suggested in the art that AF might be organized by a small number of stable rotors, e.g. centres of functional re-entrant activity, and upon ablation of the cores of these rotors in combination with pulmonary vein isolation, good treatment success rates have been reported.

Currently, electrophysiological signal acquisition is the most widely used method to monitor the spatiotemporal electrical activity and to assess the source of an arrhythmia in the human heart. For example, a catheter may be inserted in an endovascular procedure to detect the electrical activity from within the heart. Such catheter may comprise a plurality of separate electrode elements, spaced away from each other, to obtain a signal over time for a plurality of locations in or on the heart. For example, a basket catheter may comprise a plurality of electrodes, e.g. 64 electrodes, on a plurality of flexible wires. The flexible wires are configured to form a basket or balloon that can conform to the shape of (e.g. part of) the heart when inserted. The gathered data may enable a differential diagnosis and may aid in treatment planning, e.g. by identifying the source(s) of the arrhythmia to target, for example in an ablation procedure.

The acquired electrophysiological signals, e.g. obtained by a basket catheter inserted in an atrial chamber of the heart, can be analysed by phase mapping, as known in the art. Starting from a reference electrode, phase mapping assigns a phase to each electrode at each moment in time. The location of the core of a rotor involved in atrial fibrillation can then be identified by finding phase singularities in the phase mapping. For example, the U.S. Pat. No. 8,700,140 discloses such a phase mapping approach.

Alternatively, for example for anatomical re-entry characterized by stationary periodic activity, e.g. for atrial tachycardia, rotational activity around scar tissue can be visually identified in high density mapping. In such high density mapping, the heart is scanned by an electrode recording at a large number of locations, e.g. over 300 sites. Then, the local activation times may be determined and color maps may be generated to indicate the origin of the rotational activity. However, such approach relies heavily on a possibly subjective interpretation of the visualized results, and requires a large number of recorded sites.

SUMMARY OF THE INVENTION

It is an object of embodiments of the present invention to provide good and efficient means and methods for detecting points and/or regions of interest in the heart, e.g. which are indicative of cardiac arrhythmia symptoms, based on spatiotemporal electrophysiological data gathered in or on the heart.

The above objective is accomplished by a method and device according to the present invention.

It is an advantage of embodiments of the present invention that locations of rotational activity in the heart, e.g. of anatomical and/or functional re-entry, can be efficiently and/or accurately determined.

It is an advantage of embodiments of the present invention that locations of focal activity in the heart, e.g. of ectopic activity, can be efficiently and/or accurately determined.

It is an advantage of embodiments of the present invention that points and/or regions of interest with respect to arrhythmia can be identified automatically based on spatiotemporal electrophysiological data gathered in or on the heart.

It is an advantage of embodiments of the present invention that the detection of the points and/or regions of interest does not rely on subjective interpretation.

It is an advantage of embodiments of the present invention that, for a point or region involved in rotational activity in the heart, a plurality of different cycles around the point or region can be detected, e.g. detected and counted, in which a higher number of such cycles can be indicative of a higher detection confidence.

It is an advantage of embodiments of the present invention that a robust detection is provided, e.g. robust for noisy data. For example, if an electrode signal is difficult to interpret, e.g. due to a noisy reading, links via adjacent electrodes can overcome this to detect a cycle and/or a rotational activity.

It is an advantage of embodiments of the present invention that robustness against the detection of false positives can be provided. For example, prior art methods, such as phase mapping approaches, may be sensitive to false positives. For example, such false positives might arise due to variations in the distances between the electrodes and/or far field artefacts. Furthermore, such prior art methods may also be sensitive, e.g. not robust, to noisy data.

It is an advantage of embodiments of the present invention that a directed network can be used to describe electrical activity in the heart.

It is an advantage of embodiments of the present invention that it can be applied to a wide range of in-silico, experimental and clinical models of arrhythmia, leading to an improved treatment of cardiac arrhythmias.

It is an advantage of embodiments of the present invention that electrodes belonging to any cycle which are part of the same rotational activity can be determined.

It is an advantage of embodiments of the present invention that for each rotational core a region of influence can be detected.

It is an advantage of embodiments of the present invention that the dominant driving source of an arrhythmia can be determined.

It is an advantage of embodiments of the present invention that the detection of the points and/or regions of interest are independent of the type of recording system, the number of electrodes, the inter electrode distance or site of recording.

It is an advantage of embodiments of the present invention that the detection of points and/or regions or interest can be used to guide catheter ablation during an ablation procedure.

In a first aspect, the present invention relates to a device for detecting points and/or regions of rotational electrophysiological activity in or on a heart. The device comprises an input for receiving spatiotemporal electrophysiological data, e.g. gathered by a plurality of electrodes, corresponding to a plurality of spatial locations in or on the heart and a time feature extractor for providing, for each of the plurality of spatial locations, a plurality of time values indicative of times of occurrence of a predetermined feature of a corresponding plurality of electric potential waveforms at that spatial location, based on said received spatiotemporal electrophysiological data. Each electric potential waveform may refer to the electrical activity associated with a single heart pulse. For example, the plurality of electric potential waveforms may be organized as an electric signal trace, e.g. a voltage as function of time, that comprises a sequence of separate pulses, e.g. referred to as the waveforms.

The predetermined feature may be substantially the same feature that is detected in each of the waveforms and in each of the spatial locations. The predetermined feature may be an activation time, but embodiments of the present invention are not necessarily limited thereto, e.g. the feature may be a deactivation time or another waveform feature. The predetermined feature may be determined by a morphological classification representative of the waveform shape for each of the plurality of electric potential waveforms, e.g. in each location and for each heart pulse.

The device comprises a mapping unit for providing pairs of adjacent spatial locations of the plurality of spatial locations. The mapping unit may also be adapted for associating a distance, between each pair of adjacent spatial locations, with each determined pair of adjacent spatial locations.

The device comprises a directed graph generator for generating a directed graph comprising directed edges, each directed edge connecting a pair of the pairs of adjacent spatial locations in a sense of direction that is representative of a direction of propagation in time of at least one electric potential waveform of the plurality of electric potential waveforms between the pair of spatial locations, in which at least one time value of the plurality of time values for each spatial location of that pair are taken into account, e.g. at least one time value of a first spatial location of said pair and at least one time value of a second spatial location, i.e. the other spatial location, of said pair. Furthermore, the directed graph generator may also take the distance associated with each pair of the pairs of adjacent spatial locations into account.

The device comprises a topological feature analyzer for determining cycles in the directed graph. Optionally, the topological feature analyser may also be adapted for determining graph sources and/or graph sinks in the directed graph. The device comprises an output for outputting detected points and/or detected regions in or on the heart as representative of the cycles detected by the topological feature analyzer.

In a device in accordance with embodiments of the present invention, the directed graph generator may be adapted for selecting a first time value of the plurality of time values for each of the plurality of spatial locations, and, for each pair of the pairs of adjacent spatial locations, determining an absolute time difference between the selected first time value corresponding to one of that pair and the selected first time value corresponding to the other of that pair, determining a velocity by dividing the absolute time difference by the distance associated with the pair, and generating a directed edge connecting the pair in the directed graph if, and only if, the velocity satisfies a feasibility criterion.

In a device in accordance with embodiments of the present invention, the directed graph generator may be adapted for selecting a second time value, of the plurality of time values for each of the plurality of spatial locations, and, for each pair of the pairs of adjacent spatial locations, determining a first further absolute time difference between the selected first time value corresponding to one of that pair and the selected second time value corresponding to the other of that pair and/or determining a second further absolute time difference between the selected second time value corresponding to one of that pair and the selected second time value corresponding to the other of that pair. The directed graph generator may be adapted for determining a velocity by dividing the first further absolute time difference by the distance associated with the pair and/or for determining a velocity by dividing the second further absolute time difference by the distance associated with the pair. The directed graph generator may be adapted for generating a directed edge connecting the pair in the directed graph if, and only if, at least one of the determined velocities for that pair satisfies a feasibility criterion.

In a device in accordance with embodiments of the present invention, the feasibility criterion may comprise a minimum threshold and a maximum threshold, in which the feasibility criterion is satisfied if the velocity is greater than the minimum threshold and less than the maximum threshold.

In a device in accordance with embodiments of the present invention, the directed graph generator may be adapted for selecting, for each of the plurality of spatial locations, the time value as the smallest time value of the plurality of time values associated with that spatial location that is greater than a time reference point, e.g. a predetermined time reference point.

In a device in accordance with embodiments of the present invention, the directed graph generator may be adapted for generating a first intermediate directed graph based on the time reference point being a first predetermined time reference point and generating a second intermediate directed graph based on the time reference point being a second time reference point, in which the second time reference point is greater than the first predetermined time reference point, e.g. refers to a later point in time. The directed graph generator may furthermore be adapted for merging the first intermediate directed graph and the second intermediate directed graph to provide the directed graph. Thus, the directed graph generator may be adapted for selecting, for each of the plurality of spatial locations, the first time value as the smallest time value of the plurality of time values associated with that spatial location that is greater than the first time reference point, for generating the first intermediate directed graph based on the selected first time values, for selecting, for each of the plurality of spatial locations, the second time value as the smallest time value of the plurality of time values associated with that spatial location that is greater than the second time reference point, and for generating the second intermediate directed graph based on the selected second time values.

In a device in accordance with embodiments of the present invention, the directed graph generator may be adapted for merging the first intermediate directed graph and the second intermediate directed graph by a union, e.g. computing a set union, of:
the directed edges of the first intermediate directed graph, the directed edges of the second intermediate directed graph for which, for the source node of the directed edge, the selected time value based on the second time reference point is equal to the selected time value based on the first predetermined time reference point, and the directed edges of the second intermediate directed graph for which the source node of the directed edge has no corresponding outgoing directed edges in the first intermediate directed graph, but for which the selected time value based on the second time reference point is equal to the selected time value based on the first predetermined time reference point.

In a device in accordance with embodiments of the present invention, the directed graph generator may be adapted for determining the second time reference point.

Determining the second time reference point may comprise determining, for each of the plurality of spatial locations, a next time value being the smallest time value of the plurality of time values associated with that spatial location that is greater than the first time value selected for that spatial location.

Determining the second time reference point may further comprise determining, for each pair of said pairs of adjacent spatial locations, a plurality of further absolute time differences consisting of: an absolute time difference between the next time values associated with that pair, an absolute time difference between the first time values associated with that pair, an absolute time difference between the first time value of one spatial location of said pair and the next time value of the other spatial location of said pair and an absolute time difference between the next time value of said one spatial location of said pair and the first time value of said other spatial location of said pair.

Determining the second time reference point may further comprise determining, for each pair of said pairs of adjacent spatial locations, the minimal absolute difference of said further absolute time differences associated with said pair.

Determining the first intermediate graph may comprise, for each pair of said pairs of adjacent spatial locations, determining a velocity by dividing the minimal absolute time difference by the distance associated with the pair, and generating a directed edge connecting the pair in the directed graph if, and only if, this velocity satisfies the feasibility criterion. The sense of direction of such directed edge may be determined by the signed time difference associated with the minimal absolute time difference, e.g. such as to point from spatial location associated with the smaller time value to the spatial location associated with the larger time value for the smaller and the larger time value used to calculate the minimal absolute time difference.

Determining the second time reference point may further comprise determining the maximal value of said minimal absolute differences to determine the second time reference point, e.g. as the sum of the first predetermined time reference point and the maximum of said plurality of minimal absolute time differences.

In a device in accordance with embodiments of the present invention, the directed graph generator may be adapted for selecting, for each of the plurality of spatial locations, the at least one time value as the smallest time value of the plurality of time values associated with that spatial location that is greater than a predetermined time reference point, and iterating a source spatial location over the plurality of spatial locations in increasing time order defined by the time values, in which each iteration comprises:
generating the directed edges having the source spatial location of the current iteration as source based on the feasibility criterion, and
for each target spatial location that is a target of a directed edge of the directed edges generated in the current iteration, replacing the selected time value associated therewith by the smallest time value of the plurality of time values associated with the target spatial location that is greater than the selected time value associated with the source spatial location of the current iteration.

In a device in accordance with embodiments of the present invention, the directed graph generator may be adapted for selecting, for each of the plurality of spatial locations, the at least one time value as the time value or time values of the plurality of time values associated with that spatial location that are greater than a predetermined time reference point and less than the predetermined time reference point plus a predetermined time window parameter.

In a device in accordance with embodiments of the present invention, the topological feature analyzer may be adapted for determining the cycles in the directed graph using a breadth-first search algorithm.

In a device in accordance with embodiments of the present invention, the topological feature analyzer may be adapted for determining a smallest cycle of the determined cycles and determining a core point of the smallest cycle and/or a core region comprising a geometric center of the smallest cycle. The output may be adapted for outputting the core region or core point as a detected point or detected region.

In a device in accordance with embodiments of the present invention, the topological feature analyzer may be adapted for determining a largest cycle of the determined cycles around the core point or the geometrical center.

In a device in accordance with embodiments of the present invention, the topological feature analyzer may be adapted for determining a region containing all possible cycles around the point of the geometrical center, called a region of cycles.

In a device in accordance with embodiments of the present invention, the topological feature analyzer may be adapted for determining a region of influence including further spatial locations directly connected to the region of cycles in accordance with the graph, and associating this region of cycles with a region of influence In a device in accordance with embodiments of the present invention, the topological feature analyzer may be adapted for determining a plurality of regions of cycles in the directed graph, in which each region of cycles comprises a nested set of the determined cycles. The topological feature analyser may be adapted for associating a region of influence with each region of cycles by assigning the nodes of cycles in each region of cycles to the corresponding region of influence and assigning nodes, which remained unassigned to any of the regions of influence, to a region of influence based on a shortest path to any of the nodes in said region of influence. The output may be adapted for outputting the regions of influence as detected regions.

In a device in accordance with embodiments of the present invention, topological feature analyzer may be adapted for partitioning the determined cycles in a plurality of subsets, each subset being associated with a different geometric center.

In a device in accordance with embodiments of the present invention, the topological feature analyzer may be adapted for detecting a spatial location that has only outgoing directed edges associated therewith, e.g. detecting a focal source, in the directed graph and/or that has only incoming directed edges associated therewith in the directed graph, e.g. detecting a sink. The output may be adapted for outputting the detected spatial location as a detected point.

In a device in accordance with embodiments of the present invention, the input may be adapted for receiving the spatiotemporal electrophysiological data comprising a plurality of time series indicative of an electrical signal over time obtained at the corresponding plurality of locations in or on the heart.

In a device in accordance with embodiments of the present invention, the time feature extractor may be adapted for determining, from each of the plurality of time series, the at least one time value indicative of a local activation time of the at least one electric potential waveform at the spatial location corresponding to the time series.

In a device in accordance with embodiments of the present invention, the input may be adapted for receiving the spatiotemporal electrophysiological data comprising, for each of the plurality of spatial locations, the at least one time value indicative of the time of occurrence of the predetermined feature of the at least one electric potential waveform, and the feature extractor may be adapted for providing the at least one value for each of the plurality of spatial locations from the received spatiotemporal electrophysiological data.

In a device in accordance with embodiments of the present invention, the mapping unit may be adapted for storing the predetermined pairs of adjacent spatial locations and the distance between each pair of adjacent spatial locations in accordance with a predetermined spatial configuration of the plurality of electrodes.

In a device in accordance with embodiments of the present invention, the input may be adapted for receiving the spatiotemporal electrophysiological data comprising a plurality of coordinates of the plurality of spatial locations, and the mapping unit may be adapted for determining the pairs of adjacent spatial locations by applying a geometrical partitioning and/or geometrical triangulation method based on the plurality of coordinates.

In a device in accordance with embodiments of the present invention, the mapping unit may be adapted for determining the neighbouring relation by applying a predetermined threshold value, e.g. an upper threshold, to the allowed distance in between neighbouring pairs.

In a device in accordance with embodiments of the present invention, the mapping unit may be adapted for calculating a Delaunay triangulation and/or a boxed Voronoi partitioning, based on the plurality of coordinates. For example, a Voronoi partitioning may be equivalent to a Delaunay triangulation. Furthermore, a boxed Voronoi partitioning may add a further restriction to a generic Voronoi partitioning by confining a range of spatial coordinates to a box of predetermined dimensions. After determining the Voronoi regions, neighbours may be excluded, e.g. removed, when their corresponding Voronoi regions are connected by a distance exceeding the box constraint.

In a device in accordance with embodiments of the present invention, the mapping unit may be adapted for calculating, based on the plurality of coordinates, a Gabriel graph, an alpha surface reconstruction combined with a distance restriction and/or a concave-hull neighbouring relation determination method.

In a device in accordance with embodiments of the present invention, the topological feature analyzer may be adapted for validating each cycle that is determined in the directed graph to reject cycles that are inconsistent, wherein said validating of each cycle comprises:

determining, for each directed edge along said cycle, or for all but one directed edge along said cycle, a difference between a value associated with the source of that directed edge and a value associated with the target of that directed edge, in which these values comprise time values that were selected for the process of determining the directed graph or a value derived therefrom, calculating a measure of variability of said differences, and maintaining said cycle when said measure of variability is below a predetermined threshold and rejecting said cycle when said measure of variability is above said predetermined threshold.

In a device in accordance with embodiments of the present invention, the topological feature may be adapted for binning the plurality of time values selected for generating said directed graph into a plurality of discrete time bins, generating a further directed graph for detecting focal features, in which each directed edge of said directed graph is included in said further directed graph unless the source and the target of said directed edge are assigned to the same time bin, and detecting a spatial location as a point of focal electrophysiological activity if said spatial location has only outgoing edges in the further directed graph.

In a second aspect, the present invention also relates to a diagnostic workstation for reviewing electrophysiological data and/or diagnostic imaging data, in which the diagnostic workstation comprises a device in accordance with embodiments of the first aspect of the present invention.

In a third aspect, the present invention relates to a computer-implemented method for detecting points and/or regions of rotational electrophysiological activity in or on a heart. The method comprises receiving spatiotemporal electrophysiological data corresponding to a plurality of spatial locations in or on the heart, e.g. gathered by a plurality of electrodes at a plurality of spatial locations in or on the heart. The method comprises providing, for each of the plurality of spatial locations, a plurality of time values indicative of a time of occurrence of a predetermined feature of a plurality of electric potential waveforms at the spatial location. The method comprises providing pairs of adjacent spatial locations of the plurality of spatial locations. The method may also comprise associating with each determined pair of adjacent spatial locations a distance between the pair of adjacent spatial locations. The method comprises generating a directed graph comprising directed edges, each directed edge connecting a pair of the pairs of adjacent spatial locations in a sense of direction that is representative of a direction of propagation in time of at least one electric potential waveform of the plurality of electric potential waveforms between the pair of spatial locations. At least one time value of the plurality of time values for each spatial location of the pair is taken into account to generate the directed graph, e.g. at least one time value for a first spatial location of the pair and at least one time of the other spatial location of the pair. Furthermore, a distance associated with the pair of spatial locations is also taken into account to generate the directed graph. The method comprises determining cycles in the directed graph and outputting detected points and/or detected regions in or on the heart as representative of the cycles. The method optionally may also comprise determining graph sources and/or graph sinks in the directed graph and outputting detected points and/or detected regions in or on the heart as representative of the graph sources and/or graph sinks.

In a fourth aspect, the present invention relates to a computer program product for, if implemented on a processing unit, performing a method in accordance with embodiments of the third aspect of the present invention.

In a fifth aspect, the present invention relates to a data carrier storing the computer program product in accordance with embodiments of the fourth aspect of the present invention.

In a sixth aspect, the present invention relates to a transmission of a computer program product in accordance with embodiments of the fourth aspect of the present invention over a digital data communication network.

In a seventh aspect, the present invention also relates to a computer-generated image representative of detected points and/or regions in or on the heart by a method in accordance with embodiments of the third aspect of the present invention, e.g. by a computer program product in accordance with embodiments of the fourth aspect of the present invention.

In an eighth aspect, the present invention relates to a device for detecting points and/or regions of focal electrophysiological activity in or on a heart. The device comprises an input for receiving spatiotemporal electrophysiological data, e.g. gathered by a plurality of electrodes, corresponding to a plurality of spatial locations in or on the heart and a time feature extractor for providing, for each of the plurality of spatial locations, a plurality of time values indicative of times of occurrence of a predetermined feature of a corresponding plurality of electric potential waveforms at that spatial location, based on said received spatiotemporal electrophysiological data. Each electric potential waveform may refer to the electrical activity associated with a single heart pulse. For example, the plurality of electric potential waveforms may be organized as an electric signal trace, e.g. a voltage as function of time, that comprises a sequence of separate pulses, e.g. referred to as the waveforms.

The predetermined feature may be substantially the same feature that is detected in each of the waveforms and in each of the spatial locations. The predetermined feature may be an activation time, but embodiments of the present invention are not necessarily limited thereto, e.g. the feature may be a deactivation time or another waveform feature. The predetermined feature may be determined by a morphological classification representative of the waveform shape for each of the plurality of electric potential waveforms, e.g. in each location and for each heart pulse.

The device comprises a mapping unit for providing pairs of adjacent spatial locations of the plurality of spatial locations. The mapping unit may also be adapted for associating a distance, between each pair of adjacent spatial locations, with each determined pair of adjacent spatial locations.

The device comprises a directed graph generator for generating a directed graph comprising directed edges, each directed edge connecting a pair of the pairs of adjacent spatial locations in a sense of direction that is representative of a direction of propagation in time of at least one electric potential waveform of the plurality of electric potential waveforms between the pair of spatial locations, in which at least one time value of the plurality of time values for each spatial location of that pair are taken into account, e.g. at least one time value of a first spatial location of said pair and at least one time value of a second spatial location, i.e. the other spatial location, of said pair. Furthermore, the directed graph generator may also take the distance associated with each pair of the pairs of adjacent spatial locations into account.

The device comprises a topological feature analyzer for determining focal points, e.g. graph sources and/or graph sinks, in the directed graph. The device comprises an output for outputting detected points and/or detected regions in or on the heart as representative of the focal points detected by the topological feature analyzer.

In a device in accordance with embodiments of the present invention, the topological feature may be adapted for binning the plurality of time values selected for generating said directed graph into a plurality of discrete time bins, generating a further directed graph, in which each directed edge of said directed graph is included in said further directed graph unless the source and the target of said directed edge are assigned to the same time bin, and detecting a spatial location as a point of focal electrophysiological activity if, e.g. if and only if, said spatial location has only outgoing edges in the further directed graph.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 25 shows a first intermediate directed graph as can be obtained by embodiments of the present invention.

FIG. 26 shows a second intermediate directed graph as can be obtained by embodiments of the present invention.

FIG. 27 shows a merged directed graph obtained by merging the first intermediate directed graph and the second intermediate directed graph in accordance with embodiments of the present invention.

FIG. 28 shows an exemplary detected cycle to be validated in accordance with embodiments of the present invention.

FIG. 29 shows rescaled time values to be representative of a phase, in accordance with embodiments of the present invention.

FIG. 30 illustrates a variance criterion for validating a detected cycle, in accordance with embodiments of the present invention.

Figure 1:
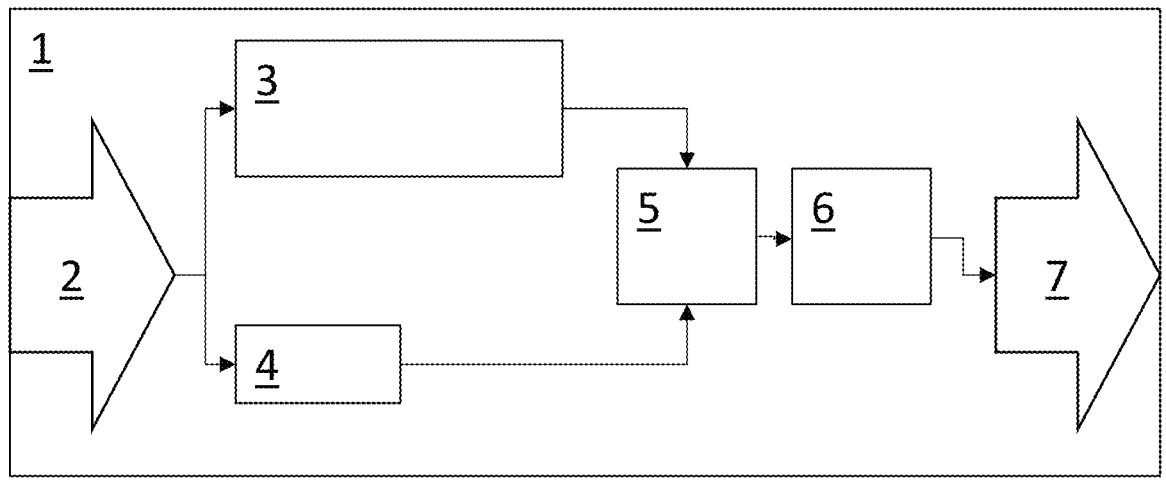
FIG. 1 schematically illustrates a device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a device for detecting points of rotational, and optionally also focal, electrophysiological activity in or on a heart and/or detecting regions of rotational and optionally also focal electrophysiological activity in or on a heart, e.g. of a human or animal subject. These points or regions of focal activity and/or rotational activity in the electric potential propagation system of the heart may be indicative of cardiac arrhythmia symptoms.

The device comprises an input for receiving spatiotemporal electrophysiological data corresponding to a plurality of spatial locations in or on the heart, e.g. gathered by a plurality of electrodes at a plurality of spatial locations in or on the heart. The device comprises a time feature extractor for providing, for each of the plurality of spatial locations, a plurality of time values indicative of times of occurrence of a predetermined feature of a plurality of electric potential waveforms at the spatial location. The device comprises a mapping unit for determining pairs of adjacent spatial locations of the plurality of spatial locations.

The device comprises a directed graph generator for generating a directed graph comprising directed edges, in which each directed edge connects a pair of the pairs of adjacent spatial locations in a sense of direction that is representative of a direction of propagation in time of at least one electric potential waveform of said plurality of electric potential waveforms between the pair of spatial locations. At least one time value of the plurality of time values for each spatial location of each pair is taken into account in generating the directed graph. Also a distance between the pair of spatial locations (for each pair) is taken into account in generating the directed graph. The device also comprises a topological feature analyzer for determining cycles in the directed graph and an output for outputting detected points and/or detected regions of interest, in or on the heart, as representative of the cycles detected by the topological feature analyzer.

Referring to FIG. 1, an exemplary device 1 in accordance with embodiments of the present invention is schematically illustrated. The device 1 is adapted for detecting points and/or regions of interest in or on a heart, e.g. which are indicative of cardiac arrhythmia symptoms, i.e. point and/or regions of rotational and/or focal electrophysiological activity.

For example, the device 1 may comprise a computer, a computing system or a processor, e.g. a general purpose computing platform specifically programmed, e.g. by a suitable executable code, for implementing the (or some) elements described hereinbelow. However, the device 1 may also comprise, additionally or alternatively, hardware specifically designed or configured for implementing the (or some) elements described hereinbelow, such as an application specific integrated circuit or a field-programmable gate array. It is appreciated that throughout the specification discussions utilizing terms such as "ascertaining," "processing," "computing," "calculating," "determining" and/or the like, refer to the action and/or processes of such computer or computing system, or similar electronic computing device, that manipulate and/or transform data represented as physical, such as electronic, quantities into other data similarly represented as physical quantities.

The term "CPU" and "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

In general, embodiments of the present invention may comprise any device capable of executing a set of instructions (sequential or otherwise) that specify actions to be taken by that device, in accordance with the features of the device as set forth hereinbelow. Thus, a typical device may be exemplified by a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. If the processing system requires a display, such a display may be included. If manual data entry is required, the processing system also includes an input device such as one or more of an alphanumeric input unit such as a keyboard, a pointing control device such as a mouse, and so forth. The term memory unit as used herein also encompasses a storage system such as a disk drive unit. The processing system in some configurations may include a sounds output device, and a network interface device. The memory subsystem may thus include a carrier medium that carries computer-readable code (e.g., software) including instructions for performing, when executed by the processing system, one of more of the methods described herein and/or implementing components of a device as described herein. The software may reside in the hard disk, or may also reside, completely or at least partially, within the RAM and/or within the processor during execution thereof by the computer system. Thus, the memory and the processor may also constitute carrier media carrying computer-readable code.

In embodiments, the device may operate as a standalone device or may be connected, e.g. networked, to other machines in a networked deployment. The device may operate in the capacity of a server or a client machine in server-client network environment, or as a peer machine in a peer-to-peer or distributed network environment. Thus, the device may also include any collection of machines that individually or jointly execute a set (or multiple sets) of instructions to perform any one or more of the methodologies discussed herein.

The device may be a personal computer (PC), a tablet PC, a Personal Digital Assistant (PDA), a cellular telephone, a web appliance, or any machine capable of executing a set of instructions (sequential or otherwise) that specify actions to be taken by that device in accordance with the features as set forth hereinbelow.

It is to be noted that the schematic diagram(s) may represent functional units of the device, which do not necessarily correspond to physically separate components of the device. Those skilled in the art will understand that many of the components of a general purpose computing platform, such as the components described hereinabove, may be included, but not explicitly shown or described in order not to obscure the description of embodiments of the present invention and any inventive aspect thereof.

The device 1 comprises an input 2 for receiving spatiotemporal electrophysiological data corresponding to a plurality of spatial locations in or on the heart, e.g. gathered by a plurality of electrodes at a plurality of spatial locations in or on the heart.

For example, the plurality of electrodes may relate to a coordinated electrode system, such as a basket electrode system. The plurality of electrodes may relate to a plurality of individual electrodes, such as intramural needle electrodes, positioned in and/or on the heart. The electrophysiological data may comprise unipolar electrode data and/or bipolar electrode data. The number of spatial locations, e.g. acquired by a corresponding number of electrodes, may be at least 3, e.g. at least 8, preferably at least 16, even more preferred at least 32, e.g. at least 64 or even at least 128. However, embodiments of the present invention are not limited by such exemplary numbers, e.g. the number of spatial locations may be even higher, e.g. 3000 or even $10^6$. The spatial locations may be arranged to cover a volume, e.g. may substantially differ from a planar arrangement such as to encompass three-dimensional positional data.

The spatiotemporal electrophysiological data may also comprise non-invasively acquired electrophysiological data corresponding to the plurality of spatial locations. For example, the spatiotemporal electrophysiological data may comprise electrocardiographic imaging data (ECGI), e.g. ICGI data on the endocardium.

The electrophysiological data may comprise data gathered by any known type of electrode system, suitable for identifying the time features, e.g. local activation times, in the plurality of spatial locations in or on the heart. For example, the electrophysiological data may comprise intramural needle data.

The input 2 may be adapted for receiving the spatiotemporal electrophysiological data comprising a plurality of time series indicative of an electrical signal over time obtained at the corresponding plurality of locations in or on the heart, e.g. for receiving time signals representative of electrical signals, such as voltage signals, over time acquired by the corresponding plurality of electrodes.

The input 2 may be adapted for receiving the spatiotemporal electrophysiological data comprising, for each of the plurality of spatial locations, the plurality of time values indicative of the times of occurrence of the predetermined feature of the plurality of electric potential waveforms. Thus, instead of receiving raw electrocardiogram signals corresponding to the plurality of spatial locations, the input may receive information derived from such raw data, e.g. in the form of the plurality of time values, e.g. local activation times.

The input 2 may be adapted for receiving the spatiotemporal electrophysiological data comprising a plurality of coordinates of the plurality of spatial locations.

For example, the input may receive positional data from a coordinated electrode system, or a pre-processor adapted for determining the position of the plurality of electrodes. Alternatively, the device may comprise a position calculator for determining the coordinates of the plurality of spatial locations, for example, by analyzing image data received by the input 2. For example, the device may be adapted for recognizing markers in an image, e.g. a three-dimensional image, such as a computed tomography, magnetic resonance imaging or echography image, in which these markers are indicative of the positions of a plurality of electrodes in the body. Alternatively, the position information may be inherently encoded in the electrophysiological data, e.g. the electrophysiological data may be structured in a regular spatial grid, e.g. corresponding to a regular three-dimensional spatial sampling. For example, the data may be obtained from an electrode system of regularly spaced electrodes, or the received data may be externally preprocessed to transform raw data into a regularly sampled grid. Instead of a regular spatial grid, the data may also be organized in a non-regular spatial configuration, in which this non-regular spatial configuration is predetermined, e.g. fixed due to a static configuration of an electrode system.

The device 1 comprises a time feature extractor 3 for providing, for each of the plurality of spatial locations, a plurality of time values indicative of a time of occurrence of a predetermined feature of a plurality of electric potential waveforms at the spatial location.

The time feature extractor 3 may be adapted for determining, from each of the plurality of time series, the plurality of time values indicative of local activation times of the plurality of electric potential waveforms at the spatial location corresponding to that time series, e.g. at the spatial location corresponding to the electrode position of the electrode corresponding to that time series. A local activation time, or a similar time value indicative of a feature of a time series fragment indicative of an electric potential waveform at a specific spatial location, may also be referred to hereinbelow as an 'arrival time'.

Figure 2:
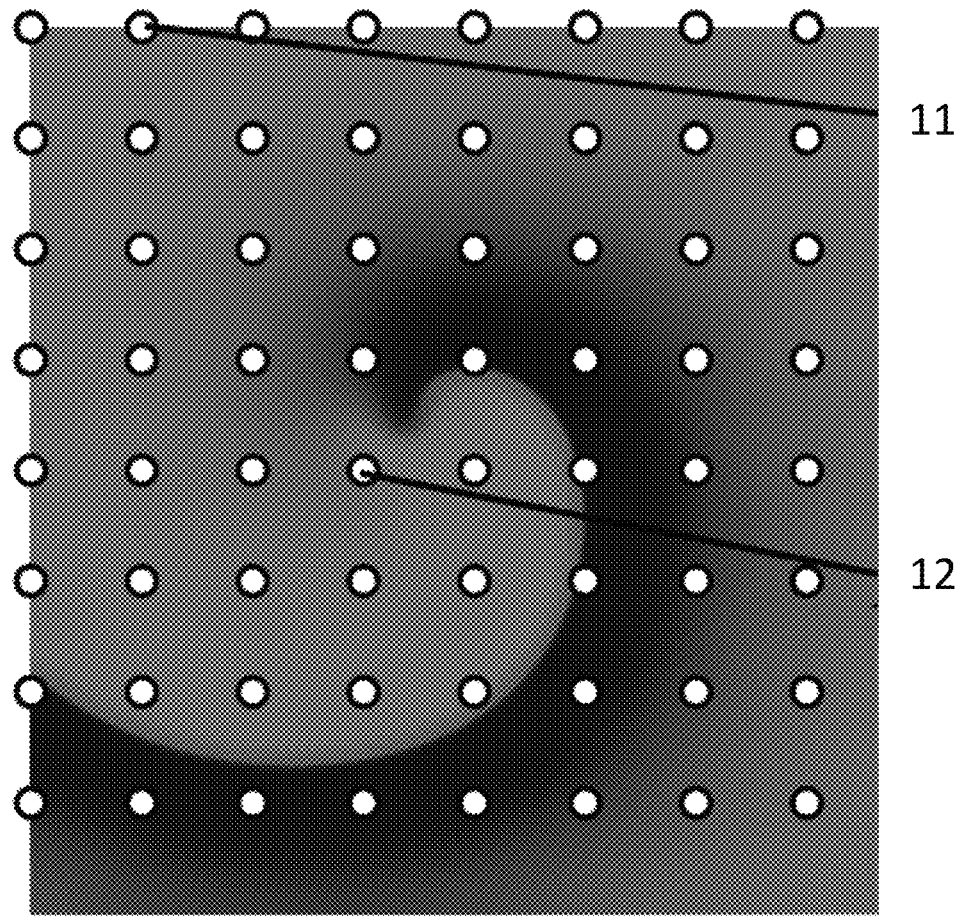
FIG. 2 shows a simulation of electrophysiological data in spatial locations defined over a regular two-dimensional grid, to illustrate embodiments of the present invention.
Figure 3:
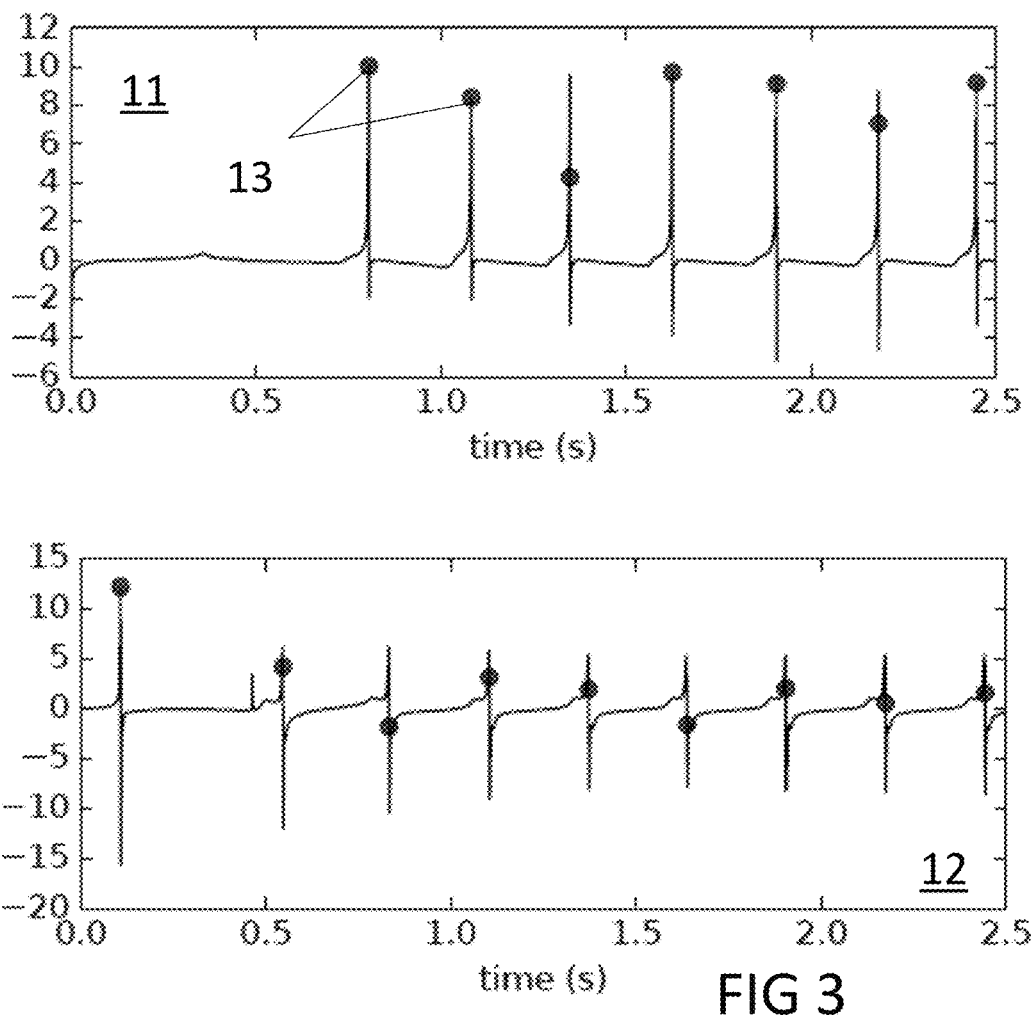
FIG. 3 shows time series corresponding to two exemplary spatial locations, to illustrate embodiments of the present invention.

FIG. 2 shows a simulation of electrophysiological data in spatial locations 11,12, . . . defined over a regular two-dimensional grid. FIG. 3 shows a time series, e.g. unipolar electrocardiogram signal (U-EGM), for two exemplary locations 11,12.

For example, the local activation time of each electric potential waveform may be determined by detecting a negative slope of the electrocardiogram signal, $-dV/dt$, which is representative of a upstroke 13 of the electric potential, as illustrated in FIG. 3. It can be observed that, due to propagation of the electric potential over the heart, different activation times (e.g. characterized by the time of an upstroke 13) corresponding to a same propagating electric potential may be determined for different locations 11, 12. Detecting such time feature of an electrocardiogram time series, e.g. a local activation time, is known in the art, and embodiments of the present invention may encompass any known method for determining such representative time reference point for an electric potential waveform. For example, it is known to use a method based on detection of a local maximum (in time) of the negative slope −dV/dt and/or of the signal V. Other methods as known in the art may comprise a center of mass approach, a non-linear energy operator, a wavelet decomposition of the signal, the U-LAT$_{Slope\text{-}hybrid}$ method and/or omnipolar mapping technology, e.g. as disclosed in Haddad et al, "Novel algorithmic methods in mapping of atrial and ventricular tachycardia," Circulation: Arrythmia and Electrophysiology, pp. CIRCEP-113, and/or in Deno et al, "Orientation-independent catheter-based characterization of myocardial activation," IEEE Transactions on Biomedical Engineering 64(5), pp. 1067-1077.

However, embodiments of the present invention are not limited to these examples. For example, other suitable methods may be found in Cantwell et al, "Techniques for automated local activation time annotation and conduction velocity estimation in cardiac mapping," Computers in biology and medicine 65, pp. 229-242.

In embodiments of the present invention, the time values, e.g. activation times, may be determined as point estimates, e.g. specific time values, or as estimation ranges, e.g. corresponding to a predetermined confidence interval for each time value.

The time feature extractor 3 may be adapted for providing the plurality of time values for each of the plurality of spatial locations from the received spatiotemporal electrophysiological data. For example, the plurality of time values, such as activation times, may be received directly by the input, for example, from a pre-processor for analysing the raw electrophysiological data. Thus the time feature extractor may, in some embodiments of the present invention, merely provide a mapping of the received pre-processed data indicative of the time values. However, in other embodiments of the present invention, the time feature extractor may comprise such pre-processor. It shall also be understood by the skilled person, that an embodiment of the present invention may be adapted for receiving and mapping such pre-processed data as well as generating the plurality of time values if raw electrophysiological data is received.

The device 1 comprises a mapping unit 4 for providing pairs of adjacent spatial locations of said plurality of spatial locations. The mapping unit 4 may also be adapted for associating a distance between each pair of adjacent spatial locations with each determined pair of adjacent spatial locations.

The mapping unit 4 may be adapted for storing the predetermined pairs of adjacent spatial locations and/or the distance between each pair of adjacent spatial locations in accordance with a predetermined spatial configuration of the plurality of electrodes. For example, the electrodes may have a fixed and/or predetermined spatial configuration, and the mapping unit may merely store an adjacency structure of the electrodes in such predetermined spatial configuration and the associated distances.

Reference to 'adjacent' are not necessarily limited to adjacencies in the sense of nearest neighbours, but may refer to a linking of all nodes in a local neighbourhood around a target node to that target node. For example, a local neighbourhood is not necessarily limited to an Euclidean ball (or disk), nor to a unit dimension. Adjacencies may be defined in reference to spatial volume, e.g. in a three-dimensional Euclidean space, but may also be defined in reference to a manifold embedded in the three-dimensional Euclidean space, e.g. on a curved surface representative of a surface of the heart. For example, the device may be adapted for taking a surface model of the heart (or a part thereof) into account, or for taking imaging data of the heart into account. Likewise, the distance between each adjacent pair of nodes may be determined as a Euclidean distance, e.g. a three-dimensional distance using a Euclidean norm, but are not necessarily limited thereto. For example, the distance may be determined over a manifold embedded in the three-dimensional coordinate space, e.g. over a curved surface representative of the surface of the heart (or part thereof).

For example, e.g. for a regular grid as illustrated in FIG. 2, the stored adjacency structure may correspond to a connection of each node to its four nearest neighbours (in a 2D grid) or 6 nearest neighbours (in a 3D grid), e.g. configured in a diamond shape pattern around the node, or of each node to its 8 direct neighbours (in a 2D grid) or 26 direct neighbours (in a 3D grid), e.g. in a box shape pattern around the node. Storage of the adjacency structure is not necessarily limited to storing an explicit map or list of the adjacencies, but may also comprise a hard implementation, e.g. a hard-coding, of the adjacencies.

The mapping unit 4 may be adapted for determining the pairs of adjacent spatial locations by applying a geometrical partitioning and/or geometrical triangulation method based on the plurality of coordinates received by the input.

The mapping unit 4 may be adapted for calculating a Delaunay triangulation, Voronoi partitioning, a boxed Voronoi partitioning, a Gabriel graph, . . . based on the plurality of coordinates. For example, in a boxed Voronoi partitioning, a confinement of the spatial coordinates to a bounding box is taken into account, such that connection of neighbours via an infinite path are avoided.

Alternatively or additionally, the mapping unit 4 may be adapted for performing an alpha surface reconstruction, e.g. optionally combined with a distance restriction. The mapping unit may also be adapted for performing another surface reconstruction technique, and/or for computing a concave-hull representation of the spatial coordinates, e.g. with or without imposing a distance restriction The device comprises a directed graph generator 5 for generating a directed graph comprising directed edges. Each directed edge connects a pair of the pairs of adjacent spatial locations, provided by the mapping unit, in a sense of direction that is representative of a direction of propagation in time of at least one electric potential waveform of the plurality of electric potential waveforms between that pair of spatial locations. It shall be understood by the skilled person that a representation in which the sense of direction is directed forward in time may be equivalent to a representation in which the sense of direction is directed backward in time. The directed graph generator 5 may be adapted for determining the sense of direction by comparing a time value of the plurality of time values for a first spatial location with a corresponding time value, e.g. which is presumed to correspond to the same propagating electric potential waveform, of the plurality of time values for a second spatial location that is adjacent to the first spatial location in accordance with a pair of adjacent locations as determined by the mapping unit, and, for example, setting the sense of direction from the lowest of these two time values to the highest of these two time values.

However, a directed edge is not necessarily created for every pair of adjacent spatial locations as determined by the mapping unit, as will be explained further hereinbelow. Thus, evidently, the sense of direction for a pair of adjacent spatial locations may, in some embodiments, only be determined in case it has been established that a directed edge for that pair is to be included in the directed graph.

For example, considering an arrival time for a propagating electric potential in two adjacent spatial locations, referred to as respectively $AT_1$ and $AT_2$, if $AT_2>AT_1$, or equivalently if $\Delta AT=AT_2-AT_1>0$, a directed edge between these two spatial locations may symbolically point from the spatial location 1 to the spatial location 2, while, if $AT_1>AT_2$, or equivalently if $\Delta AT=AT_2-AT_1<0$, a directed edge between these two spatial locations may symbolically point from the spatial location 2 to the spatial location 1.

The distance associated with each pair of the pairs of adjacent spatial locations and at least one time value of the plurality of time values for each spatial location of each pair may be taken into account by the directed graph generator 5, e.g. in generating the directed graph, e.g. in evaluating a pair (for example, for each pair) of adjacent spatial locations to determine whether a directed edge should be included in the directed graph to connect that pair of adjacent spatial locations.

The directed graph generator 5 may be adapted for selecting at least one time value of the plurality of time values for each of the plurality of spatial locations, and, for each pair of the pairs of adjacent spatial locations, determining at least one absolute time difference between respectively the, or each, selected time value corresponding to one of that pair and the, or each, selected time value corresponding to the other of that pair, e.g. a difference $\Delta AT$ as referred to in the example hereinabove.

As will be described further hereinbelow, the at least one time value may comprise multiple time values. However, it may also comprise a single time value. Examples of selecting one or more of such time values will be further explained hereinbelow. For the sake of clarity, hereinbelow some examples will be given in which the at least one time value consists of a single selected time value (e.g. a single time value for each spatial location of at least a single pair of adjacent nodes under consideration). It shall be understood that such examples, where applicable, can be extended to multiple evaluations and/or operations performed on multiple corresponding time values, e.g. in a straightforward manner and/or as explained in detail further below.

The directed graph generator may be adapted for, determining a velocity by dividing the absolute time difference, e.g. $\Delta AT$, by the distance $\Delta d$ associated with that pair, and generating a directed edge connecting that pair in the directed graph if, and only if, the velocity satisfies a feasibility criterion.

The feasibility criterion may comprise a minimum threshold and a maximum threshold, in which the feasibility criterion is satisfied if the determined velocity is greater than the minimum threshold, e.g. $CV_{min}$, and less than the maximum threshold, e.g. $CV_{max}$. Thus, the criterion may, for example, be: $\Delta d/CV_{max}<\Delta AT<\Delta d/CV_{min}$ For example, a minimum conduction velocity $CV_{min}$ may be determined and/or a maximum conduction velocity $CV_{max}$ may be determined. For example, the maximum conduction velocity may be a predetermined value, e.g. as experimentally determined, determined by simulation or determined by a theoretical conduction model of the heart. The maximum conduction velocity may be determined specifically for the heart under analysis, e.g. by statistics of direct conductivity measurements, or may be determined generally for a population or sub-population.

Likewise, the minimum conduction velocity may be a predetermined value, e.g. as experimentally determined, determined by simulation or determined by a theoretical conduction model of the heart. The minimum conduction velocity may be determined specifically for the heart under analysis, e.g. by statistics of direct conductivity measurements, or may be determined generally for a population or sub-population. For example, a first estimate of the minimum conduction velocity may be based on previous measurements.

For example, the minimum and/or maximum conduction velocity may be determined from reference data, e.g. of wave propagation during a normal sinus rhythm. Finite modelling techniques may be applied to model variations in the minimum and/or maximum velocity over a positional grid, e.g. based on such reference data. Analytical fitting techniques, such as polynomial surface fitting, may be applied to model variations in the minimum and/or maximum velocity over the positional grid. It is an advantage of the latter that it could improve model accuracy when the reference data comprises more complex activation patterns. It will be understood that, although the device in accordance with embodiments may be adapted to receive such reference data set and to determine the minimum and/or maximum thresholds from this reference data, in a device in accordance with other embodiments, the device may merely be adapted for receiving and/or storing such minimum and/or maximum velocity to be used. The minimum velocity and/or the maximum velocity may be global values, e.g. may be applied independent of the position of the spatial locations under evaluation, or may be local values, e.g. may be selected, e.g. from a reference model or lookup table, as dependent on the spatial locations under evaluation.

Furthermore, the directed graph generator 5 may be adapted for determining, or refining a predetermined initial value of, the minimum and/or maximum velocity by analysis of the electrophysiological data received via the input. For example, a variational technique may be applied to adjust the thresholds based on a quality measure applied to the directed graph generated in one run, and the adjusted thresholds may be applied in a following run. Alternatively, and/or additionally, a statistical technique may be applied to determine suitable thresholds. The device may also be adapted for adjusting one or both of the thresholds in response to a user input, e.g. such as to visually finetune the result by an experienced user.

However, the feasibility criterion may also comprise a minimum threshold and a maximum threshold, in which the feasibility criterion is satisfied if the absolute time difference is greater than the minimum threshold and less than the maximum threshold. For example, in some embodiments, the spatial locations may be organized such that neighbouring nodes are, at least approximately, uniformly spaced, e.g. in accordance with a regular grid. In such case, the distances between any pair of neighbouring spatial locations may be equal, or about equal, such that the feasibility criterion can be simplified by ignoring the impact of differences in distance between neighbouring nodes, e.g. the feasibility criterion may be directly defined as function of the absolute time difference.

The directed graph generator 5 may be adapted for selecting, for each of the plurality of spatial locations, the at least one time value as the smallest time value of the plurality of time values associated with that spatial location that is greater than a time reference point, e.g. a predetermined time reference point. Thus, a correspondence of the so selected time values to a single propagating electric potential may be assumed, or may be initially assumed.

For example, the predetermined time reference point may be selected by a user interface, e.g. to indicate a point in time in which an event of interest occurs in the electrophysiological data, e.g. the onset of an arrhythmia period. Alternatively, the predetermined time reference point may be a fixed time reference point, e.g. a fixed index such a zero time index value or a small value to discard transient effects that could invalidate an initial time frame of the received data. Alternatively, the time reference point may be determined automatically, e.g. by detecting an arrhythmia period by a global evaluation of the physiological data. Even though such examples are presented generally as alternatives, it shall be understood that a device in accordance with embodiments of the present invention can implement different alternatives, e.g. which a user can select.

Figure 4:
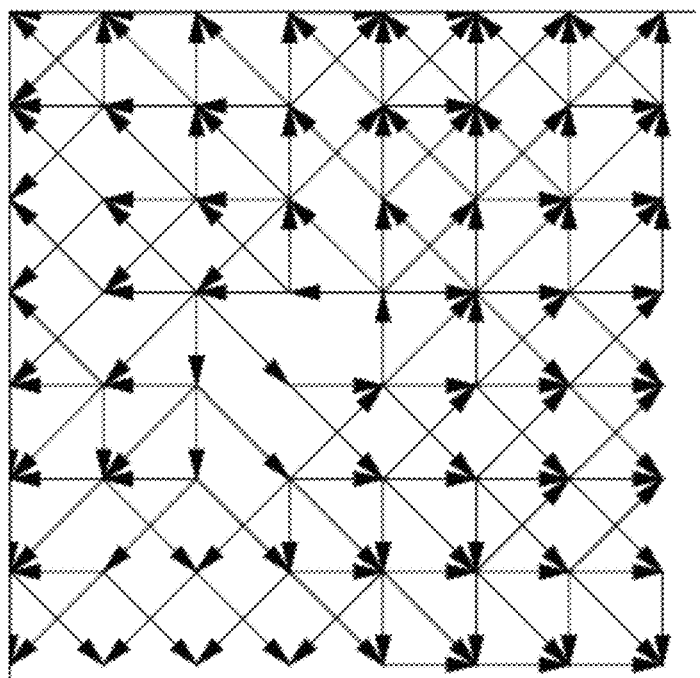
FIG. 4 shows, in an example illustrating embodiments of the present invention, a generated directed graph.

For example, FIG. 4 shows, for the exemplary propagation pattern shown in FIG. 2, a generated directed graph. In this example, the predetermined time reference point may correspond to t=1 s, e.g. the first arrival time after 1 s, such as determined by a method as illustrated in FIG. 3, may be selected for each spatial location in the exemplary regular grid to construct the directed graph.

However, while a single selected time value for each spatial location, e.g. presumably corresponding to a same propagating electric potential, was discussed hereinabove, in preferred embodiments, the directed graph generator may be adapted for selecting and processing a plurality of time values for each spatial location. For example, preferably, the directed graph generator may generate a directed graph that represents a wave propagation over a period of time which is longer than the period of an arrhythmia. Particularly, (at least) some spatial locations may be excited more than once during such period of arrhythmia.

The directed graph generator 5 may be adapted for generating a first intermediate directed graph based on the time reference point being a first predetermined time reference point and generating a second intermediate directed graph based on the time reference point being a second time reference point, e.g. a second predetermined time reference point, in which the second time reference point is greater than the first predetermined time reference point. For example, a first intermediate directed graph may be representative of the propagation of an electrical wave at a first time, while the second graph may represent the propagation of the electrical wave, or a further electrical wave, at a later time.

The difference between the second time reference point and the first predetermined time reference point does not necessarily correspond to the distance between two consecutive waves, e.g. in a single reference location. For example, the difference δt may correspond to a value that is in the range of ]0, T], where T is the period of the system. For example, the period T of the system may refer to a period of an arrhythmia. For example, the period T may be determined by subtracting two consecutive time features, e.g. consecutive arrival times, that are determined for the same spatial location. This determining of the period may comprise applying a statistical summary function, such as an averaging, of such differences over multiple points in time and/or over multiple spatial locations.

In a device in accordance with embodiments of the present invention, the directed graph generator may be adapted for determining the second time reference point by determining for each of the plurality of spatial locations a next time value being the smallest time value of the plurality of time values associated with that spatial location that is greater than the first time value selected for that spatial location, determining a plurality of further absolute time differences consisting of an absolute time difference between each pair of next time values associated with each pair of said pairs of adjacent spatial locations, an absolute time difference between each pair of first time values associated with each pair of said pairs of adjacent spatial locations and, for each pair of said pairs of adjacent spatial locations, an absolute time difference between the first time value of one spatial location of said pair and the next time value of the other spatial location of said pair and an absolute time difference between the next time value of said one spatial location of said pair and the first time value of said other spatial location of said pair. For each pair, the minimal absolute time difference of the further absolute time differences associated with that pair may be taken to determine whether a directed edge for that pair is included in the first intermediate directed graph, e.g. by calculating a velocity based on this minimal absolute time difference and testing the feasibility criterion for this velocity. Such edge may be directed in accordance with the forward sense of time between the pair, e.g. from the lowest time value to the largest time value for the time values used to calculate the further absolute time difference that was found to be the minimum absolute time difference for that pair.

Of the collective of minimal absolute time differences, the maximal value may be used to determine the second time reference point, e.g. as the sum of the first predetermined time reference point and the maximum of said plurality of minimal absolute time differences.

For example, for each spatial location i, two consecutive time values may be considered, e.g. the first time value $t_i$ and the next time value $t'_i$. Then, for each pair of adjacent spatial locations i and j, the following absolute time differences may be determined: $|t_j-t_i|$, $|t'_j-t'_i|$, $|t_j-t'_i|$ and $|t'_j-t_i|$. Then the minimal value of these four absolute time differences may be determined, and may be used to construct the directed edges of the first intermediate graph. The second time reference point may then be determined by the maximal value of the collective of minimal absolute time values. It is an advantage that a suitable second time reference point can be automatically, e.g. algorithmically, determined once a first predetermined time reference point is provided.

The directed graph generator may be adapted for merging the first intermediate directed graph and the second intermediate directed graph to provide the directed graph.

The directed graph generator may be adapted for merging the first intermediate directed graph and the second intermediate directed graph by a union of:
the directed edges of the first intermediate directed graph, and
the directed edges of the second intermediate directed graph for which, for the source node of the directed edge, the selected time value based on the second time reference point is equal to the selected time value based on the first predetermined time reference point.

For example, a directed edge of the second intermediate directed graph may also be included if the source node of the directed edge has no corresponding outgoing directed edges in the first intermediate directed graph, and if the selected time value based on the second time reference point is equal to the selected time value based on the first predetermined time reference point.

For example, suppose that, e.g. in reference to the example of FIG. 2 to FIG. 4, a spatial location $x_1$ has two outgoing arrows to spatial locations $x_5$ and $x_7$ in the first intermediate directed graph. Furthermore, suppose that, in the second intermediate directed graph, the spatial location $x_1$ has two outgoing arrows to spatial locations $x_7$, $x_8$ and $x_9$. Then, in the directed graph, e.g. the joint directed graph assembled from the first intermediate directed graph and the second intermediate directed graph, the spatial location $x_1$ may have outgoing arrows to spatial locations $x_5$, $x_7$, $x_8$ and $x_9$, if the arrival time $AT_1$ selected for the spatial location $x_1$ is equal in both intermediate graphs. Note that it is not necessary that the spatial location $x_1$ has outgoing edges in the first intermediate directed graph, e.g. in such case, the resultant directed graph would only contain the outgoing arrows from spatial location $x_1$ to the spatial locations $x_7$, $x_8$ and $x_9$.

For example, referring to FIG. 25, the directed graph generator 5 may generate a first intermediate directed graph based on a first time reference point, e.g. t=0, and, referring to FIG. 26, the directed graph generator 5 may generate a second intermediate directed graph based on a second time reference point, e.g. t=9, later than the first time reference point. The merged directed graph, see FIG. 27, may thus include the edges of the first intermediate directed graph. Furthermore, as indicated by the dashed arrow connecting the vertex having the selected time index t=60 in the first as well as in the second intermediate graph to the vertex having the selected time index t=0 in the first intermediate graph and having the selected time index t=70 in the second intermediate graph, the merged graph may also include edges of the second intermediate directed graph for which the source node has a selected time value (e.g. t=60) based on the second time reference point that is equal to the selected time value (e.g. t=60) based on the first predetermined time reference point.

It shall be noted that, even though reference is made to a first intermediate directed graph and a second intermediate directed graph, this approach can be extended to more than two intermediate directed graphs in a straightforward manner, and embodiments of the present invention are also intended to comprise such extension to a plurality of (more than two) intermediate directed graphs.

In another exemplary embodiment, the directed graph generator 5 may be adapted for selecting, for each of the plurality of spatial locations, the at least one time value as the smallest time value, of the plurality of time values associated with that spatial location, that is greater than a predetermined time reference point, and iterating a source spatial location over the plurality of spatial locations in increasing time order defined by the time values, in which each iteration comprises:
generating the directed edges having the source spatial location of the current iteration as source based on the feasibility criterion, and
for each target spatial location that is a target of a directed edge of the directed edges generated in the current iteration, replacing the selected time value associated therewith by the smallest time value of the plurality of time values associated with the target spatial location that is greater than the selected time value associated with the source spatial location of the current iteration.

For example, such approach may start from a predetermined time reference point t, e.g. substantially as described hereinabove, e.g. for the directed graph constructed without composition of intermediate directed graphs or for the first intermediate directed graph that may be used to compose the directed graph. For example, an arrival time may be initially selected for each spatial location as the smallest arrival time that is greater than t. Then, an iteration may be performed over each spatial location. To determine the directed edges, all the nodes adjacent to the node being iterated over may be assigned the smallest arrival time that is greater than the selected arrival time for that node being iterated over. A directed edge between the iteration node and an adjacent node may be generated if a feasibility criterion, as referred to hereinabove, is satisfied. Due to the time-forward assignment of the smallest arrival time that is greater than the selected arrival time for the iteration node, generated edges may be automatically outgoing edges with respect to the iteration node.

In another exemplary embodiment, the directed graph generator 5 may be adapted for selecting, for each of the plurality of spatial locations, the at least one time value as the time value or time values of the plurality of time values associated with that spatial location that are greater than a predetermined time reference point and less than the predetermined time reference point plus a predetermined time window parameter.

For example, the time window parameter L may be selected as a value that is larger than, e.g. slightly larger than, the period T, e.g. the period of a typical rotation to be analyzed. For example, starting from a predetermined time reference point t, the arrival time AT that is closest to t may be determined, e.g. $AT=t+\delta x$. Then, for all spatial locations, the arrival times that are in a range of $t+\delta x$ to $t+\delta x+L$ may be selected. Thus, a single spatial location may have more than one arrival time selected. Then, for each pair (consisting of a first node and a second node) of adjacent spatial locations being considered, the feasibility criterion may be applied to, for example, each combination of the selected time values of the first node and the selected time values of the second node.

Furthermore, embodiments of the present invention may also comprise constructing a temporal web, e.g. in which the directed graph is annotated with temporal information, e.g. in which multiple directed edges may be included between a same pair of adjacent spatial locations for different points in time. For example, such temporal web may be collapsed into a conventional directed graph by selecting a time range of interest and removing edges which are annotated with a time index outside this time range of interest. It is an advantage that such approach, may allow a quick update of the directed graph for different time frames.

The device comprises a topological feature analyzer 6 for determining cycles, graph sources and/or graph sinks in the directed graph.

Figure 5:
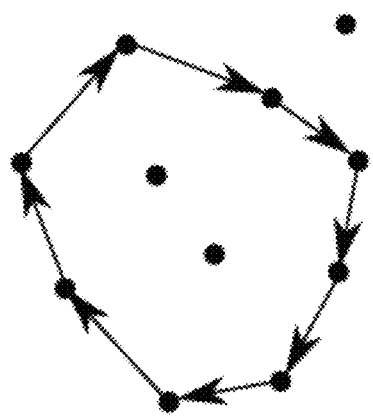
FIG. 5 illustrates a directed graph cycle, to illustrate embodiments of the present invention.

For example, a cycle, e.g. as illustrated in FIG. 5, may be determined in the directed graph.

The topological feature analyser may be adapted for determining, e.g. detecting, the cycles in the directed graph using a breadth-first search algorithm. For example, such breadth-first search algorithm, and other algorithms for determining cycles in a directed graph, embodiments not being limited to any particular method for determining such graph features as known in the art, is described by Bang-Jensen and Gutin in "Digraphs: theory, algorithms and applications," Springer Monographs in Mathematics, Springer-Verlag, London (2001). The topological feature analyser may be adapted for performing a cycle detection algorithm as disclosed in said reference work.

The topological feature analyser 6 may be adapted for validating each cycle determined, e.g. detected, in the directed graph, e.g. such as to reject cycles that are not consistent with physiological conditions, e.g. such as to keep only the cycles that are consistent with rotational activity in the heart. Validating a cycle may comprise determining, for each directed edge along the cycle, a difference between a value associated with the source of that directed edge and a value associated with the target of that directed edge, in which these values comprise time values that were selected in determining the directed graph, e.g. the first time value and/or second time value, or a value derived therefrom. For example, such selected time values may be associated with the source and target of each directed edge of the cycle, e.g. as corresponding to the time value that was selected for generating that directed edge. Therefore, a single spatial location may have two different values associated therewith, depending on whether the spatial location is considered as source or as target of two corresponding directed edges. For example, such case can arise when the directed graph was obtained by combining two intermediate graphs, as explained hereinabove.

The value derived from the selected time value may be obtained by rescaling the selected time value, e.g. such that all the selected time values considered for the cycle are rescaled to lie within a range of $2\pi$, e.g. to lie within an interval of $-\pi$ to $+\pi$. For example, the smallest selected time value $t_{min}$ associated with a spatial location on the cycle may be projected onto the value $-\pi$. Likewise, the largest selected time value $t_{max}$ associated with a spatial location on the cycle may be projected onto the value $+\pi$. For example, each selected time value $t_i$ may be transformed to the value $((t_i - t_{min})/(\text{period of CL})*2\pi) - \pi$. However, suitable alternatives for such scaling can be contemplated, e.g. for periodic data, the smallest selected time value $t_{min}$ can be projected onto the value $-\pi$ and $t_{min}$ plus the cycle period T can be projected onto the value $+\pi$. Another example may be that, e.g. for aperiodic data, the smallest selected time value $t_{min}$ can be projected onto the value $-\pi$ and the next time value, which immediately follows the selected time value when considering the plurality of time values for the same spatial location in chronological order, can be projected onto the value $+\pi$.

FIG. 28 shows an exemplary cycle, comprising a plurality of spatial locations Node 1, Node 2, . . . , Node 8 connected by a loop of directed edges. The corresponding values, expressed as phase values in the range $-\pi$ to $+\pi$ by a rescaling approach as described hereinabove, are shown in FIG. 29. The differences, e.g. as approximation of derivatives, may be calculated for the sequence of values associated with the cycle, e.g. as illustrated in FIG. 30. The variance, or similar measure of variability, of the differences may be calculated and the cycle may be maintained when this measure of variability is below a predetermined threshold and may be rejected when this measure of variability is above the predetermined threshold. Furthermore, another predetermined threshold may be applied to the difference between the first value in the sequence and the last value in the sequence, e.g. between Node 1 and Node 8 in this example. For example, if this difference is larger than $2\pi - \delta$, in which $\delta$ is a predetermined threshold, the cycle may be maintained, and otherwise rejected.

Clearly, while rescaling the time values to be representative of a phase, e.g. as described hereinabove, may be advantageously simple, it is to be noted that a same or similar validation criterion can be applied by calculating a measure of variation, e.g. a standard deviation, variance, interquartile or other such known measure, to the (e.g. non-rescaled) time values and rescaling the result of this measure of variation or rescaling the threshold that is applied in a similar manner.

The topological feature analyser 6 may be adapted for determining a smallest cycle of the determined cycles and determining a core point of the smallest cycle and/or a core region comprising a geometric centre of the smallest cycle.

The topological feature analyser 6 may be adapted for determining a largest cycle of the determined cycles around the geometric centre or core point.

A region of cycles, e.g. a set of nested cycles, can be associated with all points belonging to any possible cycle around the geometric centre, e.g. all points of the cycles of the network around that geometric centre. Thus, each region of cycles may comprise or consist of the nodes, e.g. electrode points, which are part of cycles associated with a single rotor.

For each non-marked point, i.e. for each point not belonging to a cycle, the closest 'region of cycles' can be determined in terms of network arrival time distance and can accordingly be associated with that region. As a result, for each point it is possible to determine which source excited it. The set of points that are thus associated with a single region of cycles and/or a single corresponding geometrical centre is called the 'region of influence'.

For example, determining a region of influence may comprise determining the core points for the cycles in the directed graph. Then, for each core point, all nodes may be determined which are part of all possible cycles around the core point, e.g. the cycles of the network around that core point, e.g. for which the core point lies in the area or volume encompassed by the cycle. Thus, a region of cycles can be obtained. For example, for a region of cycles, the geometric center of all cycles may be calculated belonging to that region of cycles, e.g. corresponding to a same core. The center of the rotor may be determined by applying a statistical measure of centrality, e.g. a mean or median, to the geometric centers determined for those cycles, e.g. to estimate the core point of the region of cycles more accurately.

The topological feature analyzer 6 may be adapted for partitioning the determined cycles in a plurality of subsets, each subset being associated with a different geometric center.

It is an advantage that, in this manner, different cores can be identified as centers of abnormal activity. Furthermore, the areas of influence may be determined for each such core. Therefore, an intervention can be planned to eliminate the abnormal activity caused by these core regions, taking into account the area of influence of each such core.

After exhaustively partitioning the cycles into regions of cycles, each node that has not yet been assigned to a region of cycles may be assigned to the region of cycles for which the node has the shortest path to one of the nodes of the region of cycles, e.g. determining for each region of cycles the shortest path between the unassigned node and any of the nodes of the region of cycles and selecting the region of cycles for which the smallest shortest path was found. Thus, a region of cycles and the additional nodes assigned to that region of cycles may define a region of influence.

In other words, the topological feature analyzer may be adapted for determining a plurality of regions of cycles in the directed graph, in which each region of cycles comprises a nested set of the determined cycles. The topological feature analyser may be adapted for associating a region of influence with each region of cycles by assigning the nodes of cycles in each region of cycles to the corresponding region of influence and assigning nodes, that remained unassigned to any of the regions of influence, to a region of influence based on a shortest path to any of the nodes in said region of influence.

All points inside such region of cycles or such region of influence may be assumed to be excited by the rotational activity. It is an advantage of identifying such regions of cycles and/or regions of influence that an intervention can be efficiently planned, e.g. by eliminating the activity of the core, it can be assumed that abnormal activity will cease in the area of influence, or will be excited by other sources of abnormal activity afterwards.

Figure 6:
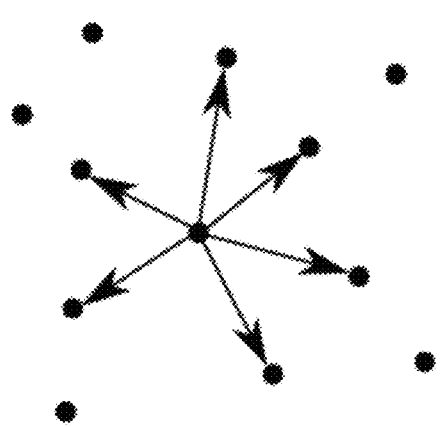
FIG. 6 illustrates a directed graph source node, to illustrate embodiments of the present invention.

The topological feature analyzer 6 may be adapted for detecting a spatial location that has only outgoing directed edges associated therewith in the directed graph and/or that has only incoming directed edges associated therewith in the directed graph. The detection of such focal features may be straightforward and can be easily and efficiently implemented, as known in the art. FIG. 6 shows an exemplary network configuration where a node has only outgoing edges.

Figure 31:
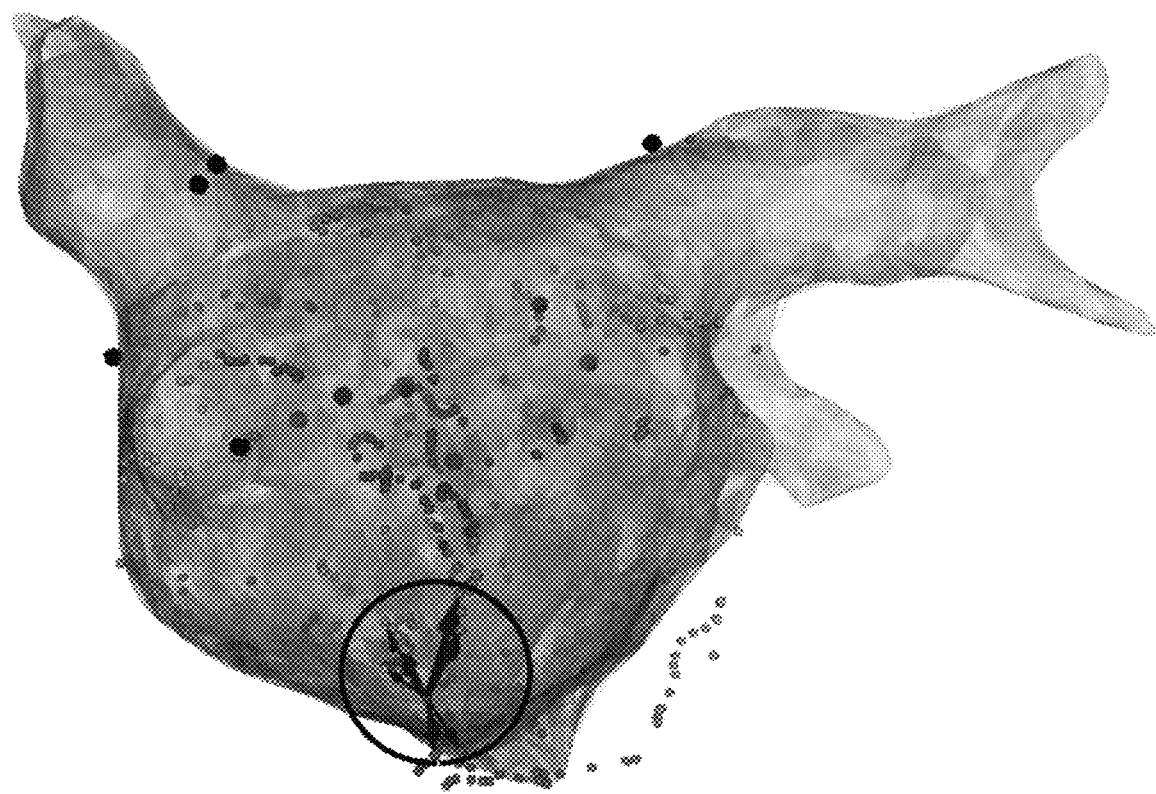
FIG. 31 illustrates a focal point detected on the heart, in accordance with embodiments of the present invention.

In order to improve the robustness of the detection of focal features, the plurality of time values may be binned. For example, a heart beat cycle may be partitioned into bins, e.g. intervals of equal length in this temporal range. For example, for a heart beat covering a range of 200 ms, 10 bins of 20 ms may be defined. The directed graph generator may be adapted for generating the directed graph (or generating another directed graph for the sole purpose of detecting focal features), in which directed edges in the directed graph, generated by an approach as described hereinabove; are removed unless the source and target of the directed edge are assigned to different bins, e.g. are not assigned to the same bin. Thus, only directed edges are considered which go from one bin to another bin. If a spatial location has only outgoing directed edges, it is detected as a focal point. FIG. 31 shows an example obtained by such approach, in which a single node as focal source has been detected in the left atrium.

The device 1 comprises an output 7 for outputting detected points and/or detected regions in or on the heart as representative of the cycles, graph sources and/or graph sinks detected by the topological feature analyzer 6.

Furthermore, a number of cycles may be counted that are detected around the same core point or region. This number may be indicative of a confidence level, e.g. a small number may indicate a likelihood of a false positive detection, whereas a larger number may represent a decreased chance of a false positive.

Figure 14:
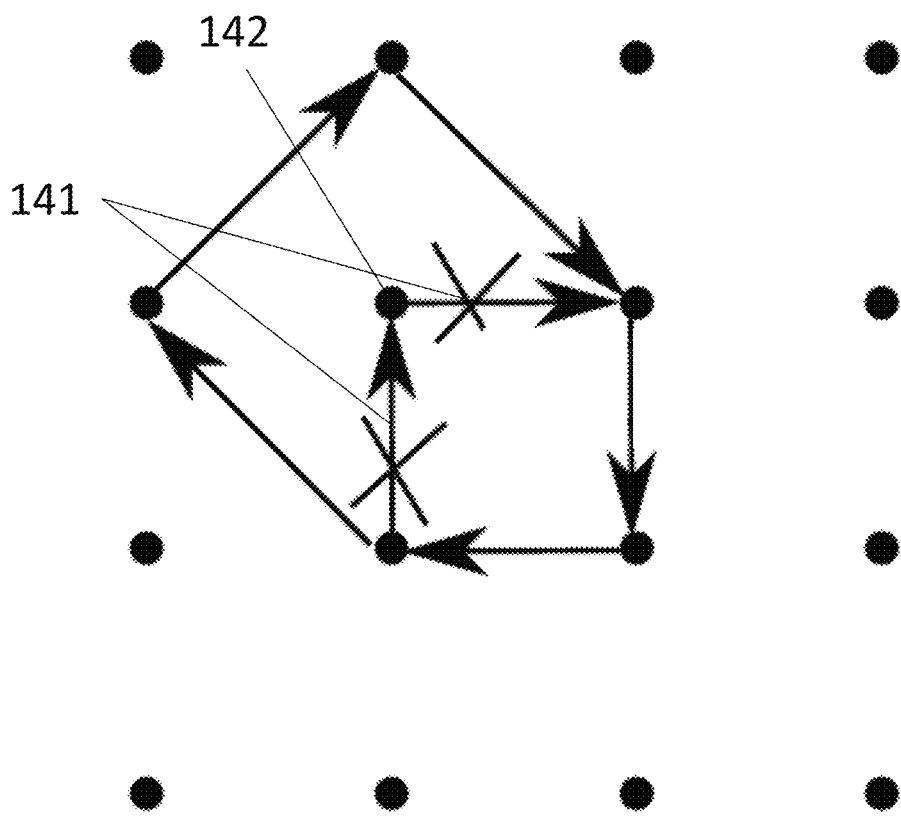
FIG. 14 schematically illustrates a resilient detection of rotational activity in the case of noisy or faulty data, relating to embodiments of the present invention.

It is also to be noted that an approach in accordance with embodiments of the present invention may be advantageously resilient against noise effects. In the example shown in FIG. 14, noise or a corrupted electrode signal may cause edges 141 to and/or from a node 142 to remain undetected. Other techniques known in the art, such as phase mapping, may detect singularities in a specific sub-grid analysis, e.g. on 2×2 grid elements. The error or failure would thus cause the singularity to remain undetected. However, in an approach in accordance with embodiments of the present invention, typically a plurality of cycles can be detected around a center of rotational activity. Thus, the rotational activity may still be detectable via a larger cycle, or a local rerouting of the cycle that would have been detected in the absence of an error or failure, e.g. the path being automatically rerouted to the next best graph for explaining the observed data.

The output 7 may be adapted for outputting the core region and/or core point, determined by the topological feature analyser 6, as a detected point or detected region.

The output 7 may be adapted for outputting the region of cycles or the region of influence as a detected region.

The output 7 may be adapted for outputting the detected spatial location that has only outgoing directed edges associated therewith in the directed graph and/or the detected spatial location that has only incoming directed edges associated therewith in the directed graph as a detected point.

The output 7 may be adapted for overlaying the detected points and/or regions on a surface model of the heart and/or on a diagnostic image of the heart.

Figure 7:
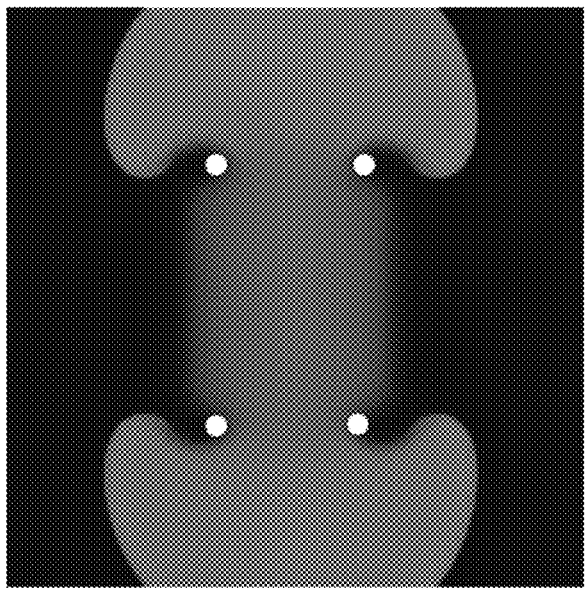
FIG. 7 illustrates a simulation of four rotors, in an example relating to embodiments of the present invention.
Figure 8:
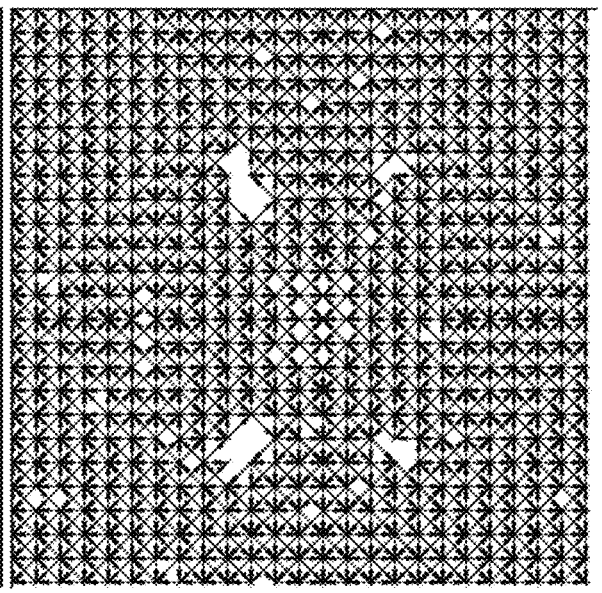
FIG. 8 shows a directed graph, corresponding to the example of FIG. 7 relating to embodiments of the present invention.

FIG. 7 shows an example in which 4 rotors are simulated. The directed graph, shown in FIG. 8, constructed in accordance with embodiments of the present invention, clearly shows cycles around the centers of these rotors (e.g. indicated by the circle markers in FIG. 7), which can be easily recognized by a digraph analysis algorithm as known in the art.

Figure 9:
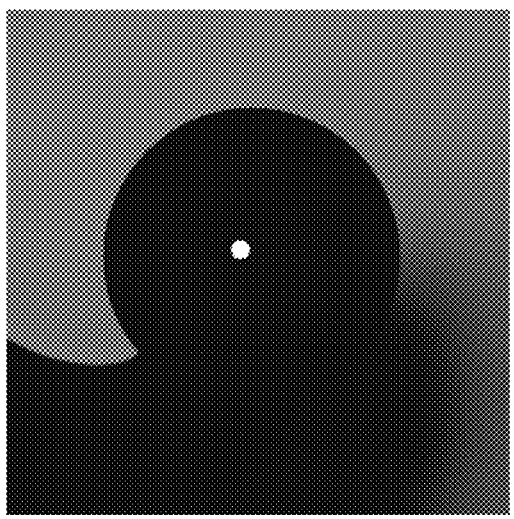
FIG. 9 shows a simulation of anatomical re-entry around a circular scar area, in an example relating to embodiments of the present invention.
Figure 10:
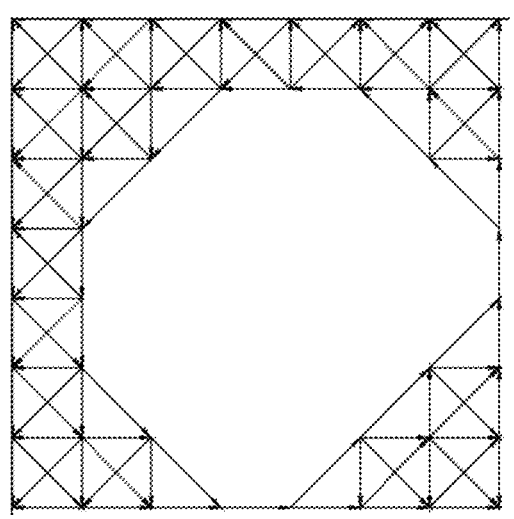
FIG. 10 shows a directed graph, corresponding to the example of FIG. 9 relating to embodiments of the present invention.

In another example, FIG. 9 shows a simulated case of anatomical re-entry around a circular scar area. The center of the scar area is indicated by a circle marker. Again, the directed graph, see FIG. 10, constructed in accordance with embodiments of the present invention, clearly reconstructs the scar region and allows to identify the center of the cycle as well as a core region, e.g. represented by the smallest detected cycle around the center.

Figure 11:
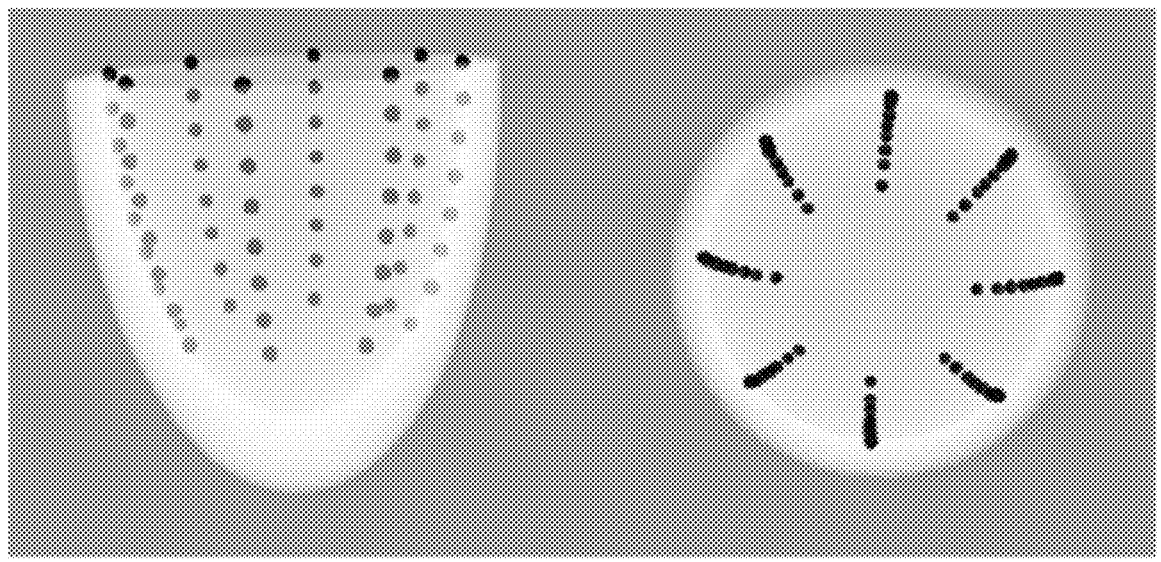
FIG. 11 shows a simulation on a three-dimensional model, as representative of a part of the heart, in an example relating to embodiments of the present invention.
Figure 12:
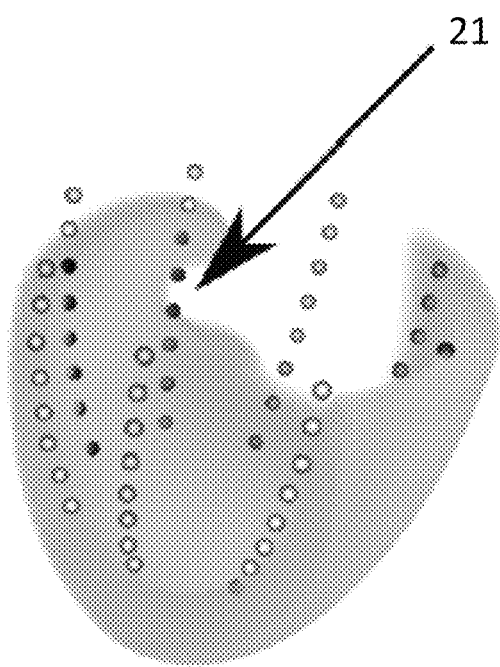
FIG. 12 shows a center of rotational activity simulated on the model of FIG. 11, in an example relating to embodiments of the present invention.
Figure 13:
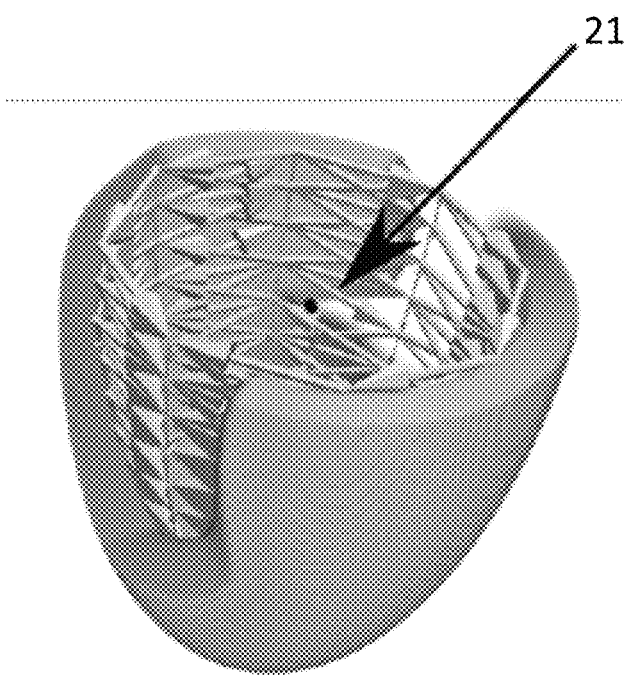
FIG. 13 shows a directed graph, corresponding to the example of FIGS. 11 and 12 relating to embodiments of the present invention.

FIG. 11 shows a simulation on a three-dimensional model, as representative of a part of the heart, in which simulated signals are acquired at the spatial locations indicated by the dot markers, e.g. in which electrodes are positioned on the simulated surface. A center 21 of rotational activity is simulated on this model, as shown in FIG. 12. It can be seen in the directed graph overlay shown in FIG. 13, constructed in accordance with embodiments, that this center of rotational activity can be identified by analysis of the graph structure.

Figure 15:
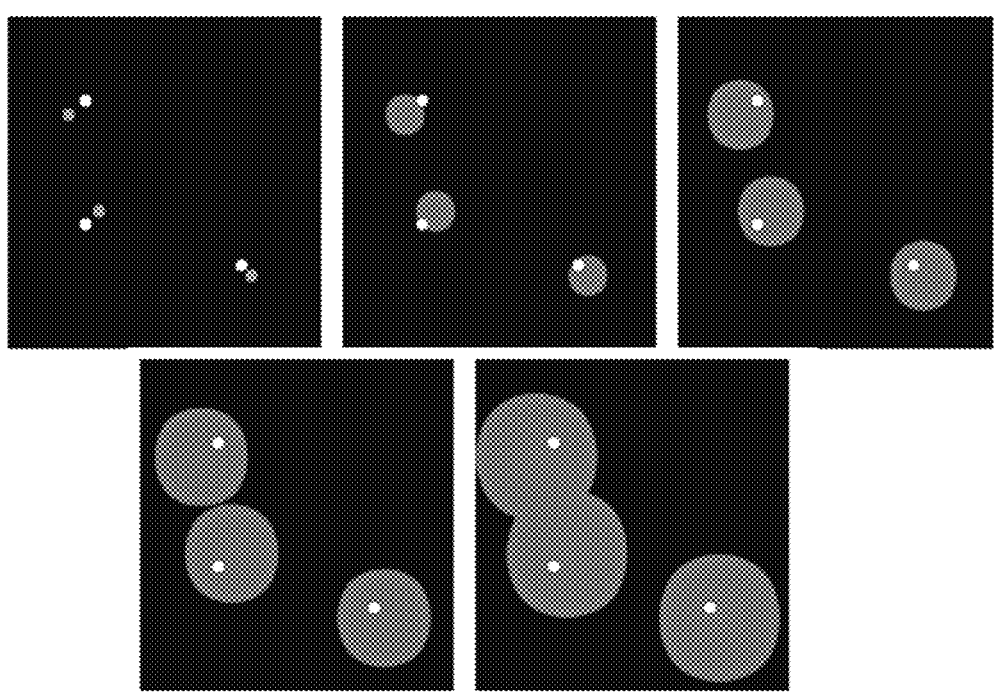
FIG. 15 illustrates simulations of focal activity and the detected points of focal activity, based on these simulations, in accordance with embodiments of the present invention.

FIG. 15 shows a plurality of simulations of focal activity, involving different sizes of affected area. The regions of focal activity are indicated by grey circles. The white dots represent the spatial locations, e.g. of the nearest electrode elements, for which the focal activity was detected in accordance with embodiments of the present invention.

In a second aspect, the present invention also relates to a diagnostic workstation for reviewing electrophysiological data and/or diagnostic imaging data, in which the diagnostic workstation comprises a device in accordance with embodiments of the first aspect of the present invention.

Figure 16:
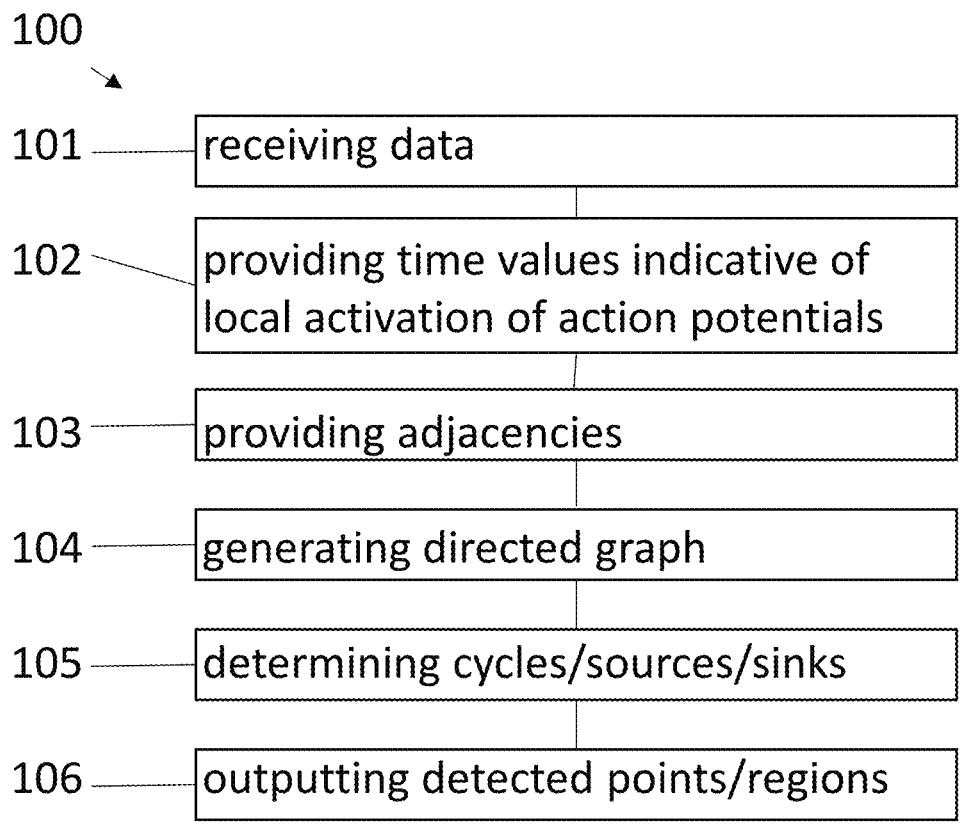
FIG. 16 illustrates an exemplary method in accordance with embodiments of the present invention.

In a third aspect, the present invention also relates to a computer-implemented method for detecting points and/or regions of rotational (and optionally also of focal) electrophysiological activity in or on a heart. Referring to FIG. 16, a method 100 in accordance with embodiments of the present invention is illustrated.

The method comprises receiving 101 spatiotemporal electrophysiological data corresponding to a plurality of spatial locations in or on the heart, e.g. gathered by a plurality of electrodes at a plurality of spatial locations in or on the heart.

The method comprises providing 102, for each of the plurality of spatial locations, a plurality of time values indicative of times of occurrence of a predetermined feature of a plurality of electric potential waveforms at that spatial location.

The method comprises providing 103 pairs of adjacent spatial locations of the plurality of spatial locations. The method may comprise associating a distance between each pair of adjacent spatial locations with each determined pair of adjacent spatial locations.

The method further comprises generating 104 a directed graph comprising directed edges, each directed edge connecting a pair of the pairs of adjacent spatial locations in a sense of direction that is representative of a direction of propagation in time of at least one electric potential waveform of the plurality of electric potential waveforms between the pair of spatial locations. At least one time value of the plurality of time values for each spatial location of each pair of spatial locations is taken into account in generating the directed graph. The distance associated with each pair of the pairs of adjacent spatial locations may also be taken into account.

The method comprises determining 105 cycles, graph sources and/or graph sinks in the directed graph, and outputting 106 detected points and/or detected regions in or on the heart as representative of the cycles, graph sources and/or graph sinks.

A method in accordance with embodiments of the present invention as described herein are, in one embodiment, performable by a machine which includes a one or more processors that accept computer-readable (also called machine-readable) code containing instructions. For any of the methods described herein, when the instructions are executed by the machine, the machine performs the method.

Further optional features, e.g. method steps, of a method in accordance with embodiments of the present invention will be clear in view of the description hereinabove relating to embodiments of the first aspect of the present invention. Furthermore, details of essential features of a method in accordance with embodiments of the present invention may also be described in greater detail in the description provided hereinabove in relation to embodiments of the present invention. Particularly, any operation performed by, or property of, a device 1, an input 2, a time feature extractor 3, a mapping unit 4 a directed graph generator 5, a topological feature analyzer 6 and/or an output 7, as described hereinabove, may be considered as a method step or method feature in a method in accordance with embodiments of the present invention.

In a fourth aspect, the present invention also relates to a computer program product for, if implemented on a processing unit, performing a method in accordance with embodiments of the third aspect of the present invention.

In a fifth aspect, the present invention also relates to data carrier storing the computer program product in accordance with embodiments of the fourth aspect of the present invention.

In a sixth aspect, the present invention also relates to a transmission of a computer program product in accordance with embodiments of the fourth aspect of the present invention over a digital data communication network.

Thus, an embodiment of a method described herein is in the form of a computer program that is executable on a processing system, e.g., on one or more processors that are part of computer, such as a device in accordance with the first aspect of the present invention. Thus, as will be appreciated by those skilled in the art, embodiments of the present invention may be embodied as a method, an apparatus such as a special purpose apparatus, an apparatus such as a data processing system, or a carrier medium, e.g. a computer program product. The carrier medium carries computer readable code for controlling a processing system to implement a method. Accordingly, aspects of the present invention may take the form of a method, an entirely hardware embodiment, an entirely software embodiment or an embodiment combining software and hardware aspects. Furthermore, the present invention may take the form of a carrier medium (e.g. a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by the machine and that cause the machine to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media may also take the form of acoustic or light waves, such as those generated during radio wave and infrared data communications. For example, the term "carrier medium" shall accordingly be taken to include, but not be limited to, solid-state memories, optical and magnetic media, and carrier wave signals.

It will be understood that the steps of methods discussed are performed in one embodiment by an appropriate processor (or processors) of a processing (e.g. computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

In a seventh aspect, the present invention also relates to a computer-generated image representative of detected points and/or regions in or on the heart by a method in accordance with embodiments of the third aspect of the present invention, e.g. by a computer program product in accordance with embodiments of the fourth aspect of the present invention.

Figure 17:
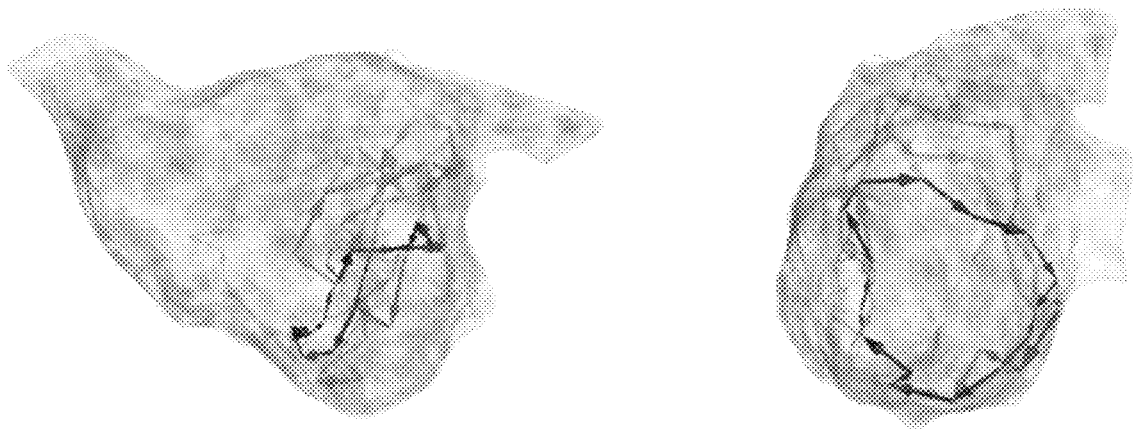
FIG. 17 shows a first further example of an analysis obtainable by embodiments of the present invention.

In a first further example, the detection of a clockwise mitral-dependent macro re-entry assisted by embodiments of the present invention is illustrated. FIG. 17 shows the detected cycles of rotational activity, overlaid on a visual representation based on imaging data, in two different projection views. The rotational activity was observed in different cycles, e.g. due to a high spatial density of sampled spatial locations, e.g. recorded by 746 electrodes. The detected core region was confirmed by a medical expert.

Figure 18:
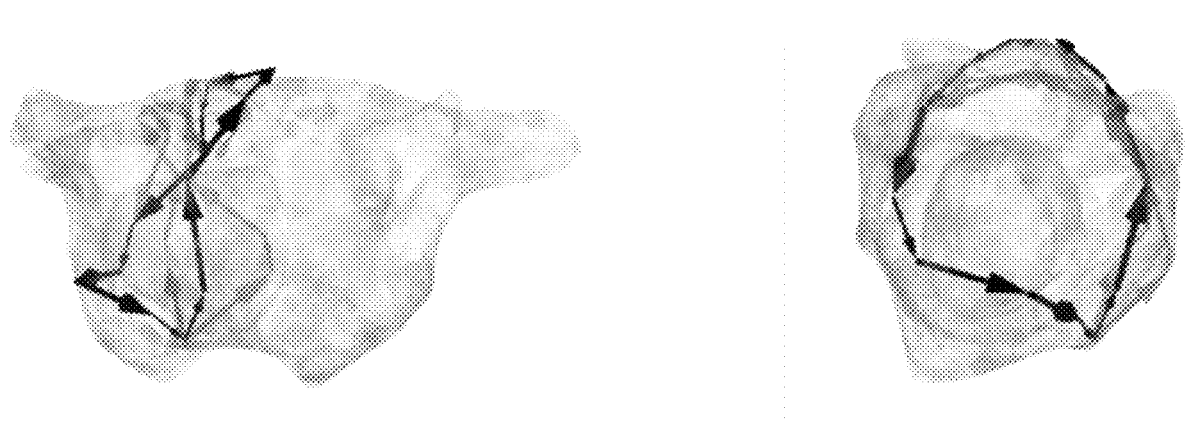
FIG. 18 shows a second further example of an analysis obtainable by embodiments of the present invention.

In a second further example, the detection of a classical roof abnormality, assisted by embodiments of the present invention, is illustrated. FIG. 18 shows the detected cycles of rotational activity, overlaid on a visual representation based on imaging data, in two different projection views. Even though the data was collected over only 177 spatial sampling points, e.g. less than in the previous example, a cycle indicative of rotational activity could be detected. The result was confirmed by a medical expert.

The method and/or device according to embodiments of the present invention can be used to determine the mechanism underlying Torsade de Pointes.

In further examples illustrating embodiments of the present invention, the accuracy of a directed graph mapping according to embodiments of the present invention in in-silico models of functional and anatomical re-entry was tested. In functional re-entry, directed graph mapping was compared to phase mapping, a widely used prior-art technique for detecting the centre of a rotor. Furthermore, for testing the accuracy of directed graph mapping in a clinical setting, 31 clinical cases of atrial tachycardia (AT) were analysed. Regular AT (in contrast to atrial fibrillation (AF)) is a clinical tachyarrhythmia in which the medical professional can be sufficiently certain regarding the underlying mechanism and location of the tachycardia. Therefore, AT was used as a gold standard for validating a directed graph approach in accordance with embodiments of the present invention.

Simulations for examples presented in the present application were done with the TNNP-computer model for human ventricular cells as described in ten Tusscher et al, "Alternans and spiral breakup in a human vertricular tissue model," Am J Physiol Heart Circ Physiol 291, H1088-H1100 (2006). The two-dimensional (2D) simulations have been carried out in an isotropic domain in a domain of 512 by 512 grid points (inter spacing of 0.25 mm) by using the explicit-Euler integration scheme for a duration of 2s. The S1S2-protocol was applied to obtain rotational activity. The whole heart simulations were done in a model of the left ventricle, and in an anatomically accurate model of the human ventricles for 20s of simulation. All simulations were performed on a GeForce GTX 680 and a GeForce GTX Titan, with single precision.

An exemplary protocol to construct a directed network graph according to embodiments of the present invention is hereinafter described. The exemplary construction of a directed network is based on a simple unipolar regular 64-electrode measuring system placed on top of a 2D rotor, as shown in FIG. 2. However, the directed graph protocol is general, and can be applied to any kind of electrode system, ranging from a basket electrode system (64/192 electrodes), intramural needle electrodes, high density grid data, simulated data (via the upstroke of the computed action potential), ECGI datasets, etc. According to embodiments of the present invention it is assumed that raw data signals or local activation time's (LAT's) are given, and the spatial coordinates of the electrode system are known. The local unipolar electrograms were computed as follows:

$$ECG(t, \vec{x}) = \int \frac{\nabla \vec{V}(t) \cdot (\vec{r} - \vec{x})}{|\vec{r} - \vec{x}|^3} d\vec{r} \qquad (1)$$

In the example presented in FIG. 2, the LAT was derived from each signal. As the signal is unipolar (U-EGM), the LAT was determined by taking the negative slope ($-dV/dt^-$) of the U-EGM as it coincides with the upstroke of the action potential (i.e., the true moment of activation). The LAT's are depicted in FIG. 3. In a next step possible neighbors are determined for each of the electrodes. These neighbors cover all possible paths where the wave can travel starting from a certain electrode. In a first example, we determined the neighbors by setting a spherical distance around a single point. Hence, a single point incorporates maximally 8 neighbors in case of the 2D grid. Similarly, for the examples with regular 3D grids, the same algorithm was taken, but now one point could have maximally 26 neighbors. For more complex geometries where the electrodes are randomly organized, like in the clinical AT cases, we applied a Delaunay triangulation and each connection was two-way. However, any other well considered neighboring technique can also be used, depending on the sparsity of the data. It is however important to keep in mind physiologically possible pathways, which are respected with the aid of this series of protocols. As a final step, the directed graph is generated. A certain time t is chosen. Starting from this time, we find $LAT_1, \ldots, LAT_n$ which are the first LAT larger than t for each electrode in our system of n electrodes. We then draw arrows as follows. Suppose electrode 1 and 2 form a pair of neighbors. Assume electrode 1 has $LAT_1$ and electrode 2 has $LAT_2$, with $LAT_2>LAT_1$, meaning the difference between the two electrodes is $\Delta LAT=LAT_2-LAT_1>0$. An arrow is drawn from electrode 1 to 2 if:

$$CV_{min} < \frac{\delta d}{\delta LAT} < CV_{max}.$$

in which $CV_{min}$ is the minimal conduction velocity, $CV_{max}$ is the maximal conduction velocity and d is the Euclidean distance between the two electrodes. This condition implies that if electrode 2 is excited by the wave propagating from electrode 1, the velocity of propagation cannot be smaller than some minimal value, and higher than a maximal value. $CV_{max}$ is usually known, e.g. can be assumed to have a predetermined value based on physical and physiological knowledge. However, estimating the $CV_{min}$ is essential for applying the equation hereinabove. In case of the simulated examples in 2D and in 3D, $CV_{min}$=0.2 mm/ms was chosen. For the clinical datasets of the LATs, as initial estimate of $CV_{min}$=0.08 mm/ms was taken, as the lowest physiological conduction velocity in human atria was determined In Konings et al. "High Density mappying of electrically induced atrial fibrillation in humans," Circulation 89, 1665-1680 (1994) to be 0.1 mm/ms. The maximal conduction velocity was set to 3.00 mm/ms. However, the results were tested by applying different values, which showed stable loops over large parameters ranges. Once this first graph was created, a second graph, graph 2, at a time t+δt was created in exactly the same way as the first graph. For the 2D example, we took δt=40 ms. Finally, these two graphs were merged in the following way. An arrow of the second graph is added to the first graph, only if the LAT of the origin of that arrow, $LAT_{i,graph2}$ was equal to the LAT of graph 1, $LAT_{i,graph1}$. This may be an important step to ensure that the network represents the correct wavefront activation. The directed graph represents the wave propagation over a period of time which is longer than the period of an arrhythmia. Pairs of neighbouring electrodes are connected by directed arrows which represent the time course of wave propagation between them. Because the time span is longer than the period of the arrhythmia some electrodes will be excited twice and both arrival times were used for composition of the graph. The resulting graph is the final directed network, as shown in FIG. 4. Once the network is created, any type of rotational activity can be found by detecting cycles in the network. A cycle is a closed directed walk without repetition of nodes. In order to find the cycles, a standard breadth-first search algorithm was used. Since the constructed network in general turns out to be rather small and very sparse, this can be done very efficiently. A first version used bounding criteria to only detect the globally smallest cycles (up to some tolerance), but it turns out that even detecting all smallest cycles through each node can be done almost instantaneously. We ran theoretical simulations on networks with 1000000 nodes, and even in these cases all cycles were found in the range of seconds. Clearly, the physical bounds on the number of electrodes that can be placed will be more limiting than the computational work that is needed to process the data. In order to find the core of any type of rotational activity, we looked for the smallest cycles in the network, and computed its geometric center. This was done by grouping all cycles that were found based on the proximity of the geometric center. If the centers lie closer to each other than a specified threshold, the cycles were considered to belong to the same core. Afterwards there was an optional pass which merges bundles of cycles if they shared nodes. The criteria for merging cycles are fully customizable. Finally, the centers of each bundle were output as the core of rotational activity. A second method, which was used for determining the center of the rotor in case of realistic datasets, was to compute the geometric center of all cycles belonging to the same core. Afterwards, the median value was taken as the true center of the rotor. In addition, only the center with the highest number of cycles was taken into account. For each network containing rotors, a 'region of cycles' and a 'region of influence' can be determined. The region of cycles contains all nodes (electrodes) which are part of cycles for a particular rotor. Second, for each non-marked point we can determine the closest 'region of cycles' in terms of network arrival time distance and related it to that region. As a result, for each point we can determine which source excited it. This is called the 'region of influence'.

In order to construct the region of influence the following algorithm was implemented. For a given network, all n cores $c_1, \ldots, c_n$ were determined. For each core, we first determined all nodes which are part of cycles of the network $(c_1, \ldots, c_n)$, i.e. the regions of cycles. Then, each node was added to the core $c_i$ to which it had the shortest path to one of its nodes in $c_i$. In this way, each core is assigned a region of influence.

For the phase mapping protocol, not being part of the invention, LAT values were used to construct the excitation patterns in phase-space. First, a sawtooth wave, with amplitude ranging from $-\pi$ to $\pi$ is constructed based on these LAT values. Afterwards, values are adapted with their $2\pi$ equivalent within the range of $-\pi$ to $\pi$ in phase-space. Next, in both x and y direction, the phases were derived and a linear combination with the Sobel (we also tested the Nabla) kernels to detect the singularities was applied. This protocol was previously presented, but instead of the Hilbert transform we made use of the sawtooth wave for the phases. In 3D, the heart was sliced in 3 orthogonal directions and the protocol was applied on each slice. However, as the shape of the ventricle model is complex, only grid points with complete circumference in the heart were taken into account, so convolution did not result in false positives on the edges. However, this did not result in detection of the filament of the rotor as the density (500 intramural points) was too sparse. A binary detection threshold was applied to the convolution, set to 95% of the maximal detected value in phase-space.

Figure 24:
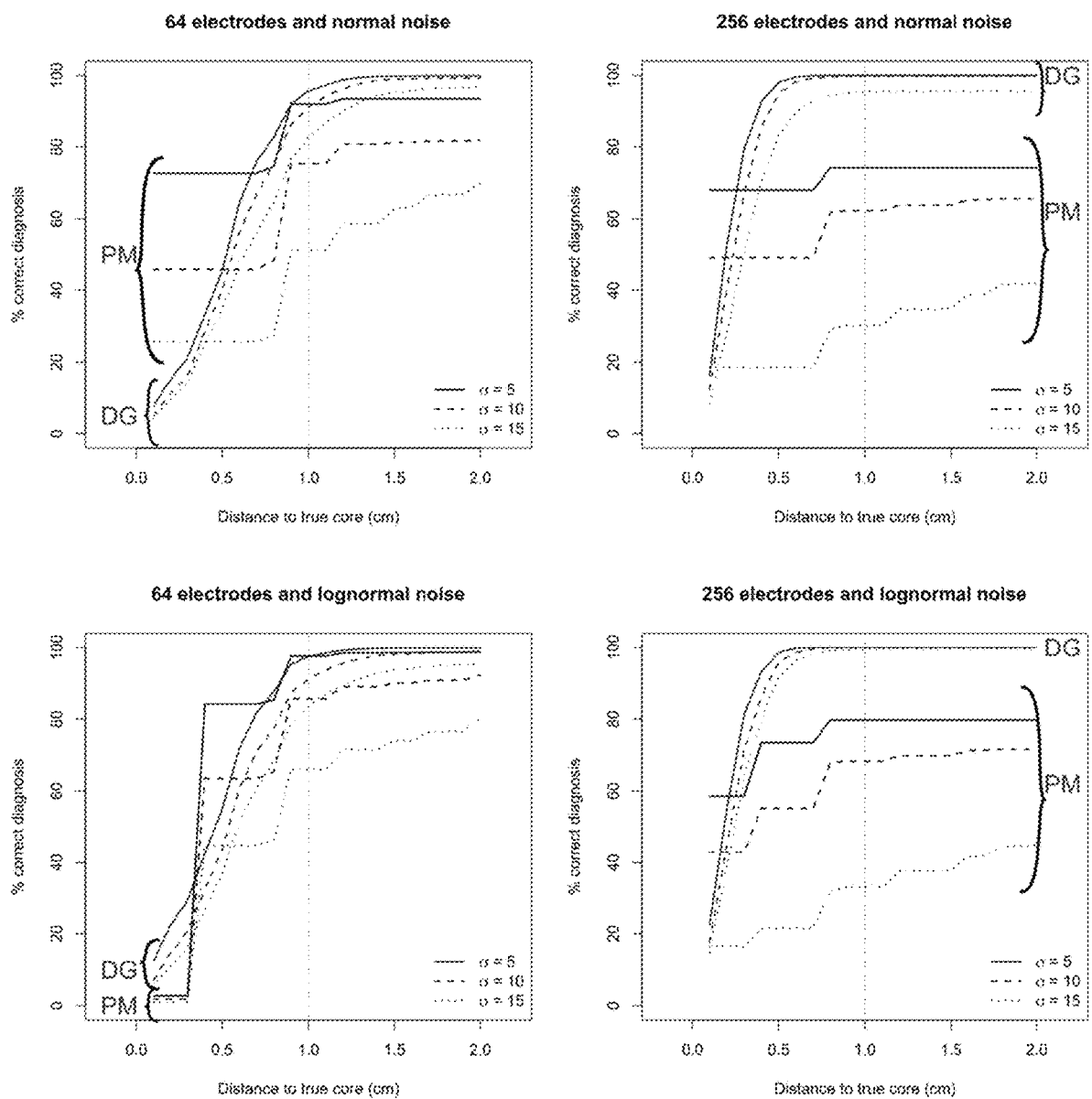
FIG. 24 shows a comparison of percentage of correct diagnoses as a function of distance to the true core for different levels of the standard deviation of the noise, for an exemplary method in accordance with embodiments of the present invention compared to a prior art phase mapping technique.

In the clinical setup, identification of LAT whether by automated algorithms or manual annotation by operators might vary due to several factors such as accuracy of the detection algorithms, operator experience, signal quality and noise. Therefore, we included LAT variation in our analysis by adding random Gaussian noise to the LATs with standard deviations $\sigma=5, 10, 15, 20, 25, 30$. Then the center of the rotor was detected with DG-mapping, in accordance with embodiments of the present invention, and with phase mapping. We classified the outcome as correct if only one single core was found within 1.0 cm of the true core. The incorrect diagnosis was classified in 3 different types: incorrect cores (i.e. cores outside a 1.0 cm radius of the true core) in combination with the correct core (error type 1), only incorrect cores (error type 2), or no cores (error type 3). For the percentage correct diagnosis p, we computed a 95% confidence interval via p+/−1.96 SE where SE is obtained from a robust sandwich estimator that accounts for the correlation structure (i.e. the 1000 replicates within one time frame are expected to be correlated). We simulated data with 64 and 256 electrodes. We also simulated noise from the skewed lognormal distribution to study the robustness of the methods for different types of noise distributions. Details are shown in FIG. 24.

For the clinical case, 29 patients undergoing ablation of symptomatic ATs were studied. Detailed endocardial mapping of ATs was performed with a single-electrode mapping and ablation catheter with a distal 3.5-mm tip and three 1-mm ring electrodes (THERMOCOOL® SMARTTOUCH ©, Biosense-Webster Inc., Diamond Bar, Calif., USA). The bipole of a decapolar coronary sinus catheter was selected as reference for activation mapping (a peak=0 ms). The following settings were applied: mapping window set to tachycardia cycle length minus 10 ms and centered at the 0 ms reference, minimum contact force of 4 g, LAT stability of 10 ms, respiratory gating enabled, and color fill calibrated at 5. Bipolar scar threshold was defined at 0.05 mV, and EGMs with bipolar voltages lower than this cutoff will therefore be automatically tagged as scar (gray zones) on the activation maps. Automated and continuous acquisition of points was done by the CONFIDENSE mapping module (Carto 3 v. 4, Biosense Webster) using the novel hybrid LAT annotation method (LATHybrid). The true tachycardia mechanism was confirmed by postpacing intervals (PPIs) 30 ms and when ablation at the targeted region (as set forward by the edited activation map) resulted in sinus rhythm or in conversion to a second tachycardia.

Figure 19:
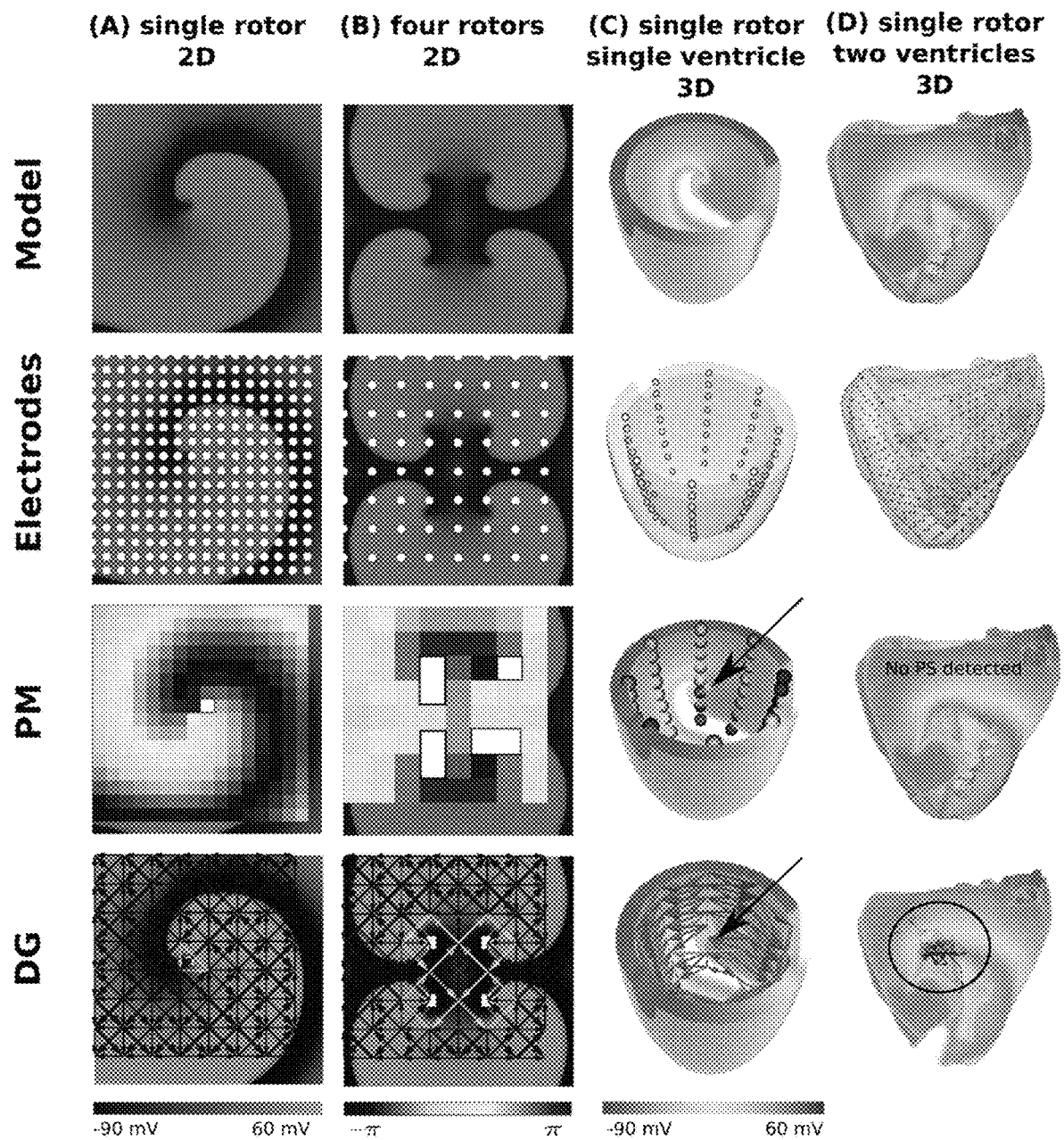
FIG. 19 shows simulation data of four in-silica models (A-D) to illustrate embodiments of the present invention and a comparison to prior art phase mapping techniques.

The accuracy of DG-mapping was tested in 4 in-silico models (see FIG. 19): a single 2D rotor (A), four 2D rotors (B), a 3D rotor in a simplified model of the left ventricle (C) and a 3D rotor in a anatomical model of both ventricles (D). In model A, we implemented 256 surface electrodes with an interspacing of electrodes of 0.8 mm mimicking experimental grid sizes. In model B and C, 64 electrodes were simulated in analogy with 64 electrode-basket catheter used in clinical practice. In model D, 500 intramural electrodes were simulated. In all cases, DG-mapping, in accordance with embodiments of the present invention, was able to detect functional reentry and able to correctly determine the location of the core of the rotor for the entire length of the simulation (2s in 2D, 20s in 3D). Phase mapping on the other hand correctly identified the phase singularity in model A, B and C, but not in model D, where a setup of 500 electrodes turned out to be insufficiently dense to determine phase singularities in 3D.

Figure 20:
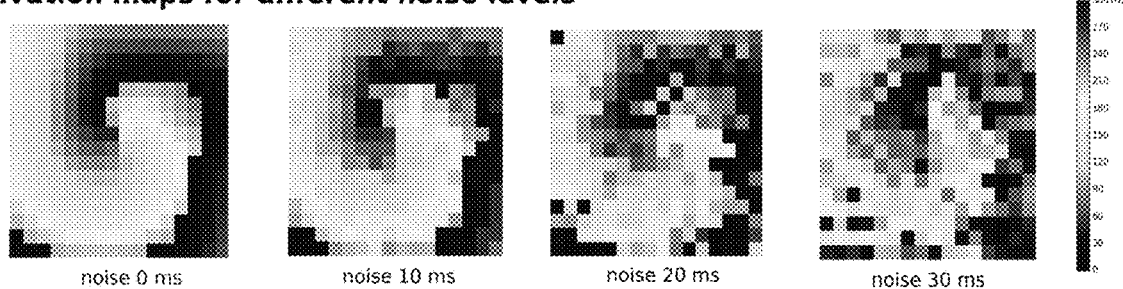
FIG. 20 shows the effect of adding noise to model A of FIG. 19 on the performance of embodiments of the present invention compared to prior art phase mapping techniques.
Figure 20:
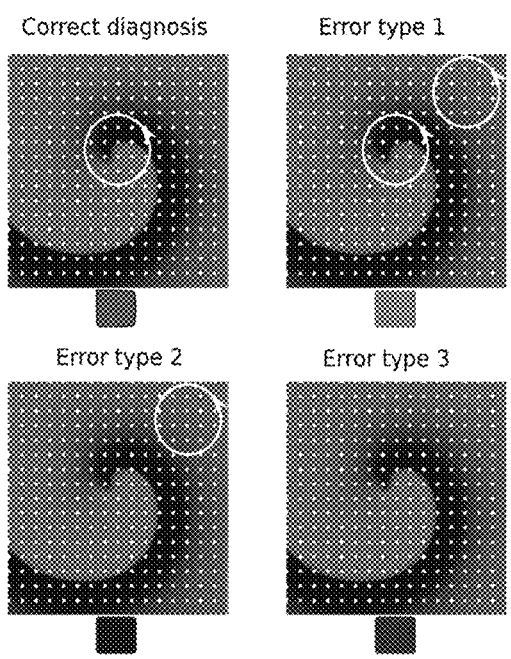
Figure 20:
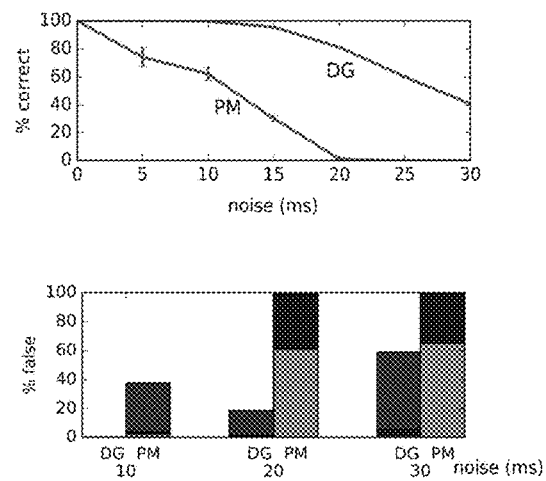

In the clinical setup, LAT's might vary due to several factors such as accuracy of the detection algorithms, operator experience, signal quality and noise. Therefore, we tested robustness of DG and phase mapping in the model of a single rotor (model A, FIG. 19) with 256 electrodes, now with adding Gaussian white noise to the LAT's. The effect on the activation maps is shown in the upper panels of FIG. 20. The performance of phase mapping and DG-mapping were compared by scoring the correctness of the diagnosis. The diagnosis was labeled correct if only one single core was found within 1.0 cm of the true core. The incorrect diagnoses were classified in 3 different types: incorrect cores (i.e. cores outside a 1.0 cm radius of the true core) in combination with the correct core (error type 1), only incorrect cores (error type 2), or no cores (error type 3). FIG. 20 shows that DG-mapping, in accordance with embodiments of the present invention, can substantially outperform phase mapping. For small variation levels (5 ms), DG-mapping is 100% accurate, while the accuracy of phase mapping decreases to 74.17%. For 15 ms, phase mapping becomes substantially less reliable (accuracy of 30.22%), while DG-mapping has an accuracy of 95.49%. For 20 ms, this difference is even more pronounced: DG-mapping has an accuracy of 81.19% while phase mapping completely breaks down to an accuracy of merely 1.08%.

In case of incorrect diagnosis, phase mapping mostly failed due to extra false cores while in the DG method the main cause of failure is the absence of any core. Similar results were obtained when comparing DG-mapping and phase mapping in the 2D single rotor model, with 64 electrodes.

To study the accuracy of DG-mapping, we tested the specificity of DG-mapping in a 2D model of focal activity with 256 electrodes (with LAT variation ranging from 5 ms to 30 ms). In none of the cases, DG-mapping identified a rotor (specificity of 100%).

Figure 21:
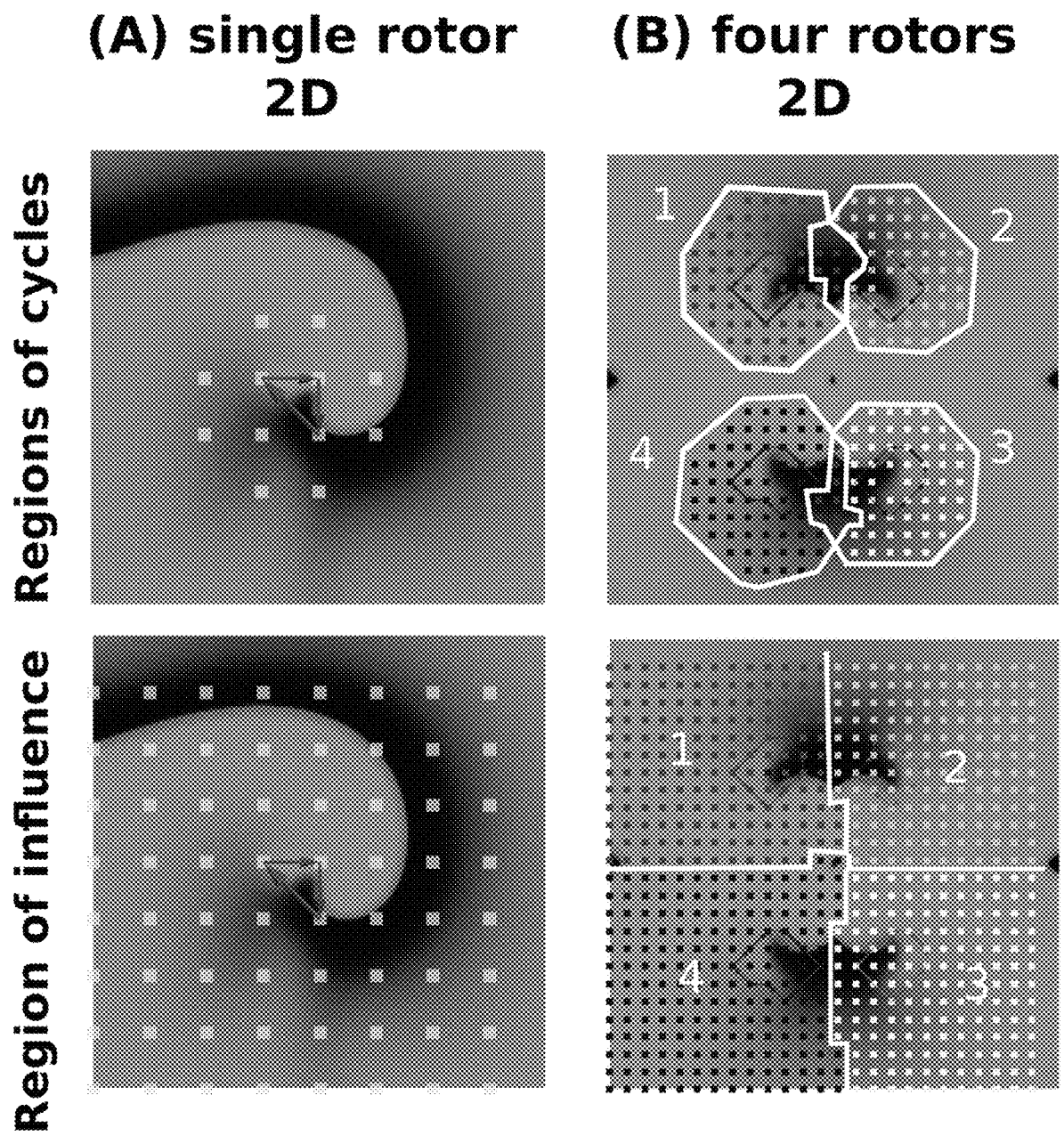
FIG. 21 shows the determination of the region of influence according to embodiments of the present invention in 2 in-silica models.

In case of normal excitation, a single source (sinus node) influences further excitation. In case of an arrhythmia with multiple sources, each source excites a given region (region of influence). We hypothesized that DG-mapping, by containing complete spatio-temporal information, can determine the area of influence. This concept was evaluated in model A and model B (see FIG. 21). Obviously, in model A, the region of influence spans the entire set of electrodes. In contrast, in the four 2D rotors (model B), one can appreciate the area of influence for each given rotor.

Figure 22:
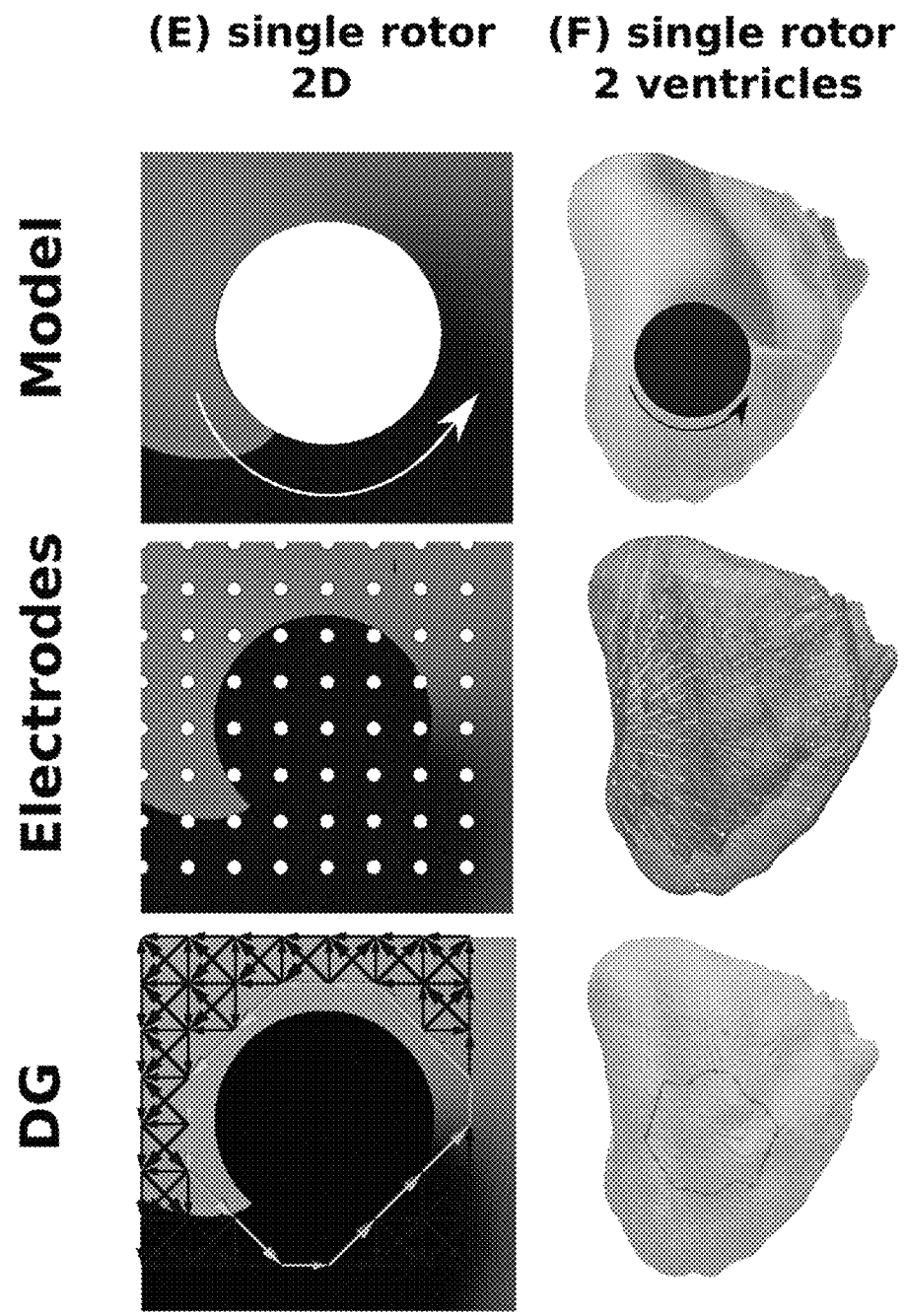
FIG. 22 shows simulation data of 2 models of anatomical re-entry (E-F) to illustrate embodiments of the present invention.

DG-mapping was validated in 2 models of anatomical reentry: a 2D single anatomical circuit with 64 electrodes (model E) and a 3D anatomical reentry with 1710 intramural points in the anatomical model of the ventricles (model F). In both models, DG-mapping correctly identified the reentrant path around the obstacles for the entire length of the simulation (20s). The shortest reentry paths were plotted with the largest number of cycles for the same core, see FIG. 22. In both models, phase mapping could not detect any phase singularities.

Figure 23:
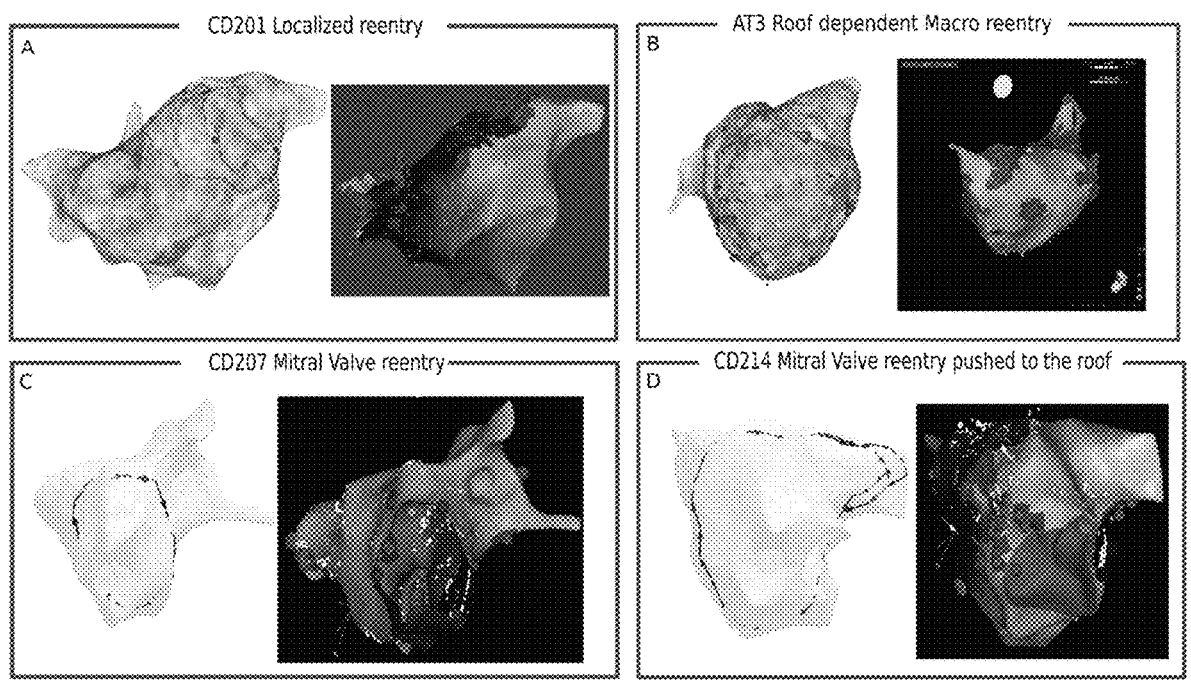
FIG. 23 shows four examples of clinical AT cases to illustrate embodiments of the present invention.

We retrospectively and blindly analyzed 31 cases of regular atrial tachycardia (AT). All patients were mapped with the CARTO system and ablation was based on the interpretation of color coded activation maps guided by the CONFIDENSE module and the embedded Wavefront annotation algorithm to identify LATs. The accuracy of DG-mapping (presence or absence of rotational activity and location of the circuit) was compared to the gold standard diagnosis, i.e. the type of arrhythmia and location of the circuit as determined by the electrophysiologist based on the activation map and the ablation result. According to the gold standard, 21 cases were macro reentry, 5 localized reentry and 5 focal activity with centrifugal activation. Compared to the gold standard, DG-mapping pointed to the same mechanism and location in 28 cases (90.3%, 95% exact binomial confidence interval 74.2%-98%). Representative cases of the accuracy of DG-mapping are given in FIG. 23: Case A (CD201), localized reentry at the anterior wall; Case B (AT3) large macro reentry at the roof traveling up on the anterior wall, and down on the posterior wall; case C (CD207) a clockwise mitral valve reentry; case D (CD214) clockwise mitral valve reentry, but pushed away from the mitral annulus. In 3 cases (9.7%), the diagnosis of DG-mapping did not fully match with the gold standard diagnosis: in 2 cases, the gold standard diagnosis was double loop reentry, whereas DG-mapping identified only one single loop. In the other case, the gold standard diagnosis of AT was focal tachycardia, whereas DG-mapping identified localized reentry as the same spot. In all 3 cases, however, the diagnosis of DG-mapping would have led to the correct ablation target.

A device and/or method according to embodiments of the present invention could be applied to mapping of ventricular tachycardia. In particular, a device and/or method according to embodiments of the present invention could be used in hemodynamically unstable ventricular tachycardia, by allowing mapping of activation with a limited number measuring points.

The invention claimed is:

1. A device for detecting points and/or regions of rotational electrophysiological activity in or on a heart, said device comprising:

an input for receiving spatiotemporal electrophysiological data corresponding to a plurality of spatial locations in or on the heart;

a time feature extractor for providing, based on said received spatiotemporal electrophysiological data, for each of said plurality of spatial locations, a plurality of time values indicative of a time of occurrence of a predetermined feature of a plurality of electric potential waveforms at said spatial location;

a mapping unit for providing pairs of adjacent spatial locations of said plurality of spatial locations;

a directed graph generator for generating a directed graph comprising directed edges, each directed edge connecting a pair of said pairs of adjacent spatial locations in a sense of direction that is representative of a direction of propagation in time of at least one electric potential waveform of the plurality of electric potential waveforms between said pair of spatial locations, and wherein a distance associated with each pair of said pairs of adjacent spatial locations and at least one time value of said plurality of time values for each spatial location of said pair are taken into account to generate said directed graph;

a topological feature analyzer for determining cycles in said directed graph; and an output for outputting detected points and/or detected regions in or on said heart as representative of said cycles detected by said topological feature analyzer;

wherein said directed graph generator is adapted for selecting a first time value of said plurality of time values for each of said plurality of spatial locations, and, for each pair of said pairs of adjacent spatial locations, determining an absolute time difference between the first time value corresponding to one of said pair and the first time value corresponding to the other of said pair, determining a velocity by dividing said absolute time difference by said distance associated with said pair, and generating a directed edge connecting said pair in said directed graph if, and only if, said velocity satisfies a feasibility criterion; and/or wherein said directed graph generator is adapted for binning the plurality of time values selected for generating said directed graph into a plurality of discrete bins, generating a further directed graph for detecting focal features, in which each directed edge of said directed graph is included in said further directed graph unless a source and a target of said directed edge are assigned to the same discrete time bin, and detecting a spatial location as a point of focal electrophysiological activity if said spatial location has only outgoing edges in the further directed graph; and/or wherein said topological feature analyzer is adapted for validating each cycle that is determined in the directed graph to reject cycles that are inconsistent, wherein said validating of each cycle comprises:

determining, for each directed edge along said cycle, or for all but one directed edge along said cycle, a difference between a value associated with a source of that directed edge and a value associated with a target of that directed edge, in which these values comprise time values that were selected for the process of determining the directed graph or a value derived therefrom, calculating a measure of variability of said differences, and maintaining said cycle when said measure of variability is below a predetermined threshold and rejecting said cycle when said measure of variability is above said predetermined threshold.

2. The device of claim 1, wherein said mapping unit is adapted for associating a distance between each pair of adjacent spatial locations with said pair of adjacent spatial locations, and wherein said directed graph generator is adapted for generating said directed graph by taking said distance associated with each pair of said pairs of adjacent spatial locations into account.

3. The device of claim 1, wherein said feasibility criterion comprises a minimum threshold and a maximum threshold, said feasibility criterion being satisfied if said velocity is greater than said minimum threshold and less than said maximum threshold.

4. The device of claim 1, wherein said directed graph generator is adapted for selecting, for each of said plurality of spatial locations, said first time value as a smallest time value of the plurality of time values associated with that spatial location that is greater than a time reference point.

5. The device of claim 4, wherein said directed graph generator is adapted for generating a first intermediate directed graph based on said time reference point being a first predetermined time reference point and generating a second intermediate directed graph based on said time reference point being a second time reference point, said second time reference point being greater than said first predetermined time reference point, said directed graph generator being furthermore adapted for merging said first intermediate directed graph and said second intermediate directed graph to provide said directed graph, wherein said directed graph generator is adapted for merging said first intermediate directed graph and said second intermediate directed graph by a union of:

the directed edges of the first intermediate directed graph, and the directed edges of the second intermediate directed graph for which, for the source node of the directed edge, said selected first time value based on said second time reference point is equal to said selected first time value based on said first predetermined time reference point.

6. The device of claim 5, wherein said directed graph generator is adapted for determining said second time reference point by:

determining, for each of said plurality of spatial locations, a next time value being the smallest time value of the plurality of time values associated with that spatial location that is greater than the first time value selected for that spatial location, determining, for each pair of said pairs of adjacent spatial locations, a plurality of further absolute time differences consisting of: an absolute time difference between the next time values associated with said pair, an absolute time difference between the first time values associated with said pair, an absolute time difference between the first time value of one spatial location of said pair and the next time value of the other spatial location of said pair and an absolute time difference between the next time value of said one spatial location of said pair and the first time value of said other spatial location of said pair, determining, for each pair of said pairs of adjacent spatial locations, a minimal absolute difference of said further absolute time differences associated with said pair, and determining a maximal value of said minimal absolute differences to determine the second time reference point.

7. The device of claim 4, wherein said directed graph generator is adapted for selecting, for each of said plurality of spatial locations, said at least one time value as the smallest time value of the plurality of time values associated with that spatial location that is greater than said time reference point, and iterating a source spatial location over said plurality of spatial locations in increasing time order defined by said time values, in which each iteration comprises:

generating said directed edges having the source spatial location of the current iteration as source based on said feasibility criterion, and for each target spatial location that is a target of a directed edge of said directed edges generated in the current iteration, replacing said selected time value associated therewith by the smallest time value of the plurality of time values associated with said target spatial location that is greater than the selected time value associated with said source spatial location of the current iteration.

8. The device of claim 1, wherein said directed graph generator is adapted for selecting, for each of said plurality of spatial locations, said at least one time value as the time value or time values of the plurality of time values associated with that spatial location that are greater than a predetermined time reference point and less than the predetermined time reference point plus a predetermined time window parameter.

9. The device of claim 1, wherein said topological feature analyzer is adapted for determining a smallest cycle of said determined cycles and determining a core point of said smallest cycle and/or a core region comprising a geometric center of said smallest cycle, wherein said output is adapted for outputting said core region or core point as a detected point or detected region.

10. The device of claim 9, wherein said topological feature analyzer is adapted for determining a largest cycle of said determined cycles around said center.

11. The device of claim 9, wherein said topological feature analyzer is adapted for determining a region of cycles comprising all possible cycles around said geometric center.

12. The device of claim 1, wherein said topological feature analyzer is adapted for determining a plurality of regions of cycles in said directed graph, in which each region of cycles comprises a nested set of said determined cycles, and wherein said feature analyzer is adapted for associating a region of influence with each region of cycles by assigning the nodes of cycles in each region of cycles to the corresponding region of influence and assigning nodes that remained unassigned to any of the regions of influence to a region of influence based on a shortest path to any of the nodes in said region of influence.

13. The device of claim 1, wherein said topological feature analyzer is adapted for detecting a spatial location that has only outgoing directed edges associated therewith in said directed graph and/or that has only incoming directed edges associated therewith in said directed graph, and wherein said output is adapted for outputting said detected spatial location as a detected point.

14. A diagnostic workstation for reviewing electrophysiological data and/or diagnostic imaging data, said diagnostic workstation comprising a device in accordance with claim 1.

15. A computer-implemented method for detecting points and/or regions of rotational electrophysiological activity in or on a heart, said method comprising:
  receiving spatiotemporal electrophysiological data corresponding to a plurality of spatial locations in or on the heart;
  providing, based on said electrophysiological data, for each of said plurality of spatial locations, a plurality of time values indicative of a time of occurrence of a predetermined feature of a plurality of electric potential waveforms at said spatial location;
  providing pairs of adjacent spatial locations of said plurality of spatial locations;
  generating a directed graph comprising directed edges, each directed edge connecting a pair of said pairs of adjacent spatial locations in a sense of direction that is representative of a direction of propagation in time of at least one electric potential waveform of the plurality of electric potential waveforms between said pair of spatial locations, and wherein a distance associated with each pair of said pairs of adjacent spatial locations and at least one time value of said plurality of time values for each spatial location of said pair are taken into account to generate said directed graph;
  determining cycles in said directed graph; and
  outputting detected points and/or detected regions of interest in or on said heart as representative of said cycles;
    wherein said directed graph generator is adapted for selecting a first time value of said plurality of time values for each of said plurality of spatial locations, and, for each pair of said pairs of adjacent spatial locations, determining an absolute time difference between the first time value corresponding to one of said pair and the first time value corresponding to the other of said pair, determining a velocity by dividing said absolute time difference by said distance associated with said pair, and generating a directed edge connecting said pair in said directed graph if, and only if, said velocity satisfies a feasibility criterion; and/or
  wherein said directed graph generator is adapted for binning the plurality of time values selected for generating said directed graph into a plurality of discrete bins, generating a further directed graph for detecting focal features, in which each directed edge of said directed graph is included in said further directed graph unless a source and a target of said directed edge are assigned to the same discrete time bin, and detecting a spatial location as a point of focal electrophysiological activity if said spatial location has only outgoing edges in the further directed graph; and/or
  wherein a topological feature analyzer is adapted for validating each cycle that is determined in the directed graph to reject cycles that are inconsistent, wherein said validating of each cycle comprises:
    determining, for each directed edge along said cycle, or for all but one directed edge along said cycle, a difference between a value associated with the source of that directed edge and a value associated with the target of that directed edge, in which these values comprise time values that were selected for the process of determining the directed graph or a value derived therefrom,
    calculating a measure of variability of said differences, and
    maintaining said cycle when said measure of variability is below a predetermined threshold and rejecting said cycle when said measure of variability is above said predetermined threshold.

16. A computer program product for, if implemented on a processing unit, performing the method in accordance with claim 15.

* * * * *